(12) United States Patent
Ferrera et al.

(10) Patent No.: US 10,383,751 B2
(45) Date of Patent: Aug. 20, 2019

(54) METHOD AND APPARATUS FOR OCCLUSION REMOVAL

(71) Applicant: Perflow Medical Ltd., Tel-Aviv (IL)

(72) Inventors: David Ferrera, Coto De Caza, CA (US); Avraham Rapaport, Tel-Aviv (IL); Gilad Cibulski, Zur-Moshe (IL); Allon Reiter, Tel-Aviv (IL)

(73) Assignee: Perflow Medical Ltd., Natania (IL)

( * ) Notice: Subject to any disclaimer, the term of this patent is extended or adjusted under 35 U.S.C. 154(b) by 475 days.

(21) Appl. No.: 14/372,778

(22) PCT Filed: Jan. 17, 2013

(86) PCT No.: PCT/US2013/021942
§ 371 (c)(1),
(2) Date: Jul. 17, 2014

(87) PCT Pub. No.: WO2013/109756
PCT Pub. Date: Jul. 25, 2013

(65) Prior Publication Data
US 2014/0343585 A1    Nov. 20, 2014

Related U.S. Application Data

(60) Provisional application No. 61/693,026, filed on Aug. 24, 2012, provisional application No. 61/679,508, (Continued)

(51) Int. Cl.
*A61F 2/90* (2013.01)
*A61B 17/221* (2006.01)
(Continued)

(52) U.S. Cl.
CPC ............ *A61F 2/90* (2013.01); *A61B 17/1214* (2013.01); *A61B 17/12118* (2013.01);
(Continued)

(58) Field of Classification Search
CPC ............ A61B 17/22032; A61B 17/221; A61B 17/3205; A61B 17/32056;
(Continued)

(56) References Cited

U.S. PATENT DOCUMENTS 4,890,611 A * 1/1990 Monfort ............... A61B 17/221
600/587
5,217,484 A 6/1993 Marks
(Continued)

FOREIGN PATENT DOCUMENTS

CN     102014772    4/2011
EP     2265195      12/2010
(Continued)

OTHER PUBLICATIONS

Notice of Reason for Rejection dated Oct. 25, 2016 From the Japan Patent Office Re. Application No. 2016-006194.
(Continued)

*Primary Examiner* — Elizabeth Houston
*Assistant Examiner* — Kankindi Rwego

(57) ABSTRACT

A system for removing a thrombus. The system includes an expandable device that maintains axially fixed engagement with the thrombus. The expandable device applies a first force to the thrombus according to surrounding vessel size. The expandable device applies a second force to the thrombus according to an increased vessel size to maintain axially fixed engagement.

38 Claims, 23 Drawing Sheets

Related U.S. Application Data filed on Aug. 3, 2012, provisional application No. 61/587,617, filed on Jan. 17, 2012.

(51) Int. Cl.

| | |
|---|---|
| *A61B 17/3207* | (2006.01) |
| *A61B 17/12* | (2006.01) |
| *A61F 2/966* | (2013.01) |
| *A61B 17/22* | (2006.01) |
| *A61B 17/3209* | (2006.01) |
| *A61F 2/82* | (2013.01) |

(52) U.S. Cl.
CPC .... *A61B 17/221* (2013.01); *A61B 17/320725* (2013.01); *A61F 2/966* (2013.01); *A61B 2017/22034* (2013.01); *A61B 2017/32096* (2013.01); *A61F 2002/823* (2013.01); *A61F 2250/0098* (2013.01)

(58) Field of Classification Search
CPC .. A61B 2017/2202; A61B 2017/22031; A61B 2017/22034; A61B 2017/22035; A61B 2017/22081; A61B 2017/22094; A61B 2017/2212; A61B 2017/2215; A61B 2017/2217; A61B 2017/320716; A61B 2017/320725; A61B 2017/320741; A61B 17/22031; A61B 17/320725; A61B 17/3207; A61B 17/12118; A61B 17/1214; A61B 2017/22037; A61B 2017/22039; A61B 2017/22041; A61B 2017/22042; A61B 2017/22044; A61B 2017/22045; A61B 2017/22047; A61B 2017/320733; A61F 2/90; A61F 2/966
See application file for complete search history.

(56) References Cited

U.S. PATENT DOCUMENTS

| | | | |
|---|---|---|---|
| 5,354,310 A | 10/1994 | Garnic et al. | |
| 5,527,326 A * | 6/1996 | Hermann | A61B 17/221 606/159 |
| 5,888,291 A | 3/1999 | Chopin et al. | |
| 5,954,745 A | 9/1999 | Gertler et al. | |
| 6,780,196 B2 | 8/2004 | Chin et al. | |
| 2002/0165574 A1 | 11/2002 | Ressemann et al. | |
| 2005/0119684 A1 | 6/2005 | Guterman et al. | |
| 2009/0292297 A1* | 11/2009 | Ferrere | A61B 17/221 606/127 |
| 2009/0292307 A1 | 11/2009 | Razack | |
| 2010/0114017 A1 | 5/2010 | Lenker et al. | |
| 2010/0318178 A1 | 12/2010 | Rapaport et al. | |
| 2011/0009950 A1 | 1/2011 | Grandfield et al. | |
| 2011/0060212 A1* | 3/2011 | Slee | A61B 17/221 600/424 |
| 2011/0160742 A1 | 6/2011 | Ferrera et al. | |
| 2011/0213403 A1* | 9/2011 | Aboytes | A61F 2/013 606/194 |
| 2011/0264132 A1 | 10/2011 | Strauss et al. | |
| 2012/0123466 A1* | 5/2012 | Porter | A61B 17/221 606/200 |
| 2013/0030460 A1* | 1/2013 | Marks | A61B 17/221 606/200 |

FOREIGN PATENT DOCUMENTS

| | | |
|---|---|---|
| JP | 2003-033359 | 2/2003 |
| JP | 2011-516183 | 5/2011 |
| WO | WO 2009/124288 | 10/2009 |
| WO | WO 2010/075565 | 7/2010 |
| WO | WO 2010/146581 | 12/2010 |
| WO | WO 2012/120490 | 9/2012 |
| WO | WO 2013/109756 | 7/2013 |

OTHER PUBLICATIONS

Translation of Notice of Reason for Rejection dated Oct. 25, 2016 From the Japan Patent Office Re. Application No. 2016-006194.
International Search Report and the Written Opinion dated May 13, 2013 From the International Searching Authority Re. Application No. PCT/US2013/021942.
International Search Report and the Written Opinion dated Mar. 25, 2013 From the International Searching Authority Re. Application No. PCT/US2013/021746.
Supplementary European Search Report and the European Search Opinion dated Oct. 8, 2015 From the European Patent Office Re. Application No. 13738707.2.
Notice of Reasons for Rejection dated Nov. 29, 2016 From the Japan Patent Office Re. Application No. 2014-553409 and Its Translation Into English. (7 Pages).
Notification of Office Action and Search Report dated Jul. 27, 2016 From the State Intellectual Property Office of the People's Republic of China Re. Application No. 201380012864.9 and Its Translation of Office Action Into English.
Notification of Office Action dated Dec. 23, 2015 From the State Intellectual Property Office of the People's Republic of China Re. Application No. 201380012864.9.
Translation dated Jan. 10, 2016 of Notification of Office Action dated Dec. 23, 2015 From the State Intellectual Property Office of the People's Republic of China Re. Application No. 201380012864.9.
Notification of Office Action dated Feb. 6, 2017 From the State Intellectual Property Office of the People's Republic of China Re. Application No. 201380012864.9 and Its Translation Into English. (16 Pages).
International Preliminary Report on Patentability dated Oct. 2, 2014 From the International Bureau of WIPO Re. Application No. PCT/US2013/021942.
Translation of Notice of Reasons for Rejection dated Sep. 19, 2017 From the Japan Patent Office Re. Application No. 2014-553409. (10 Pages).
Communication Pursuant to Article 94(3) EPC dated Apr. 18, 2017 From the European Patent Office Re. Application No. 13738707.2. (3 Pages).
Restriction Official Action dated Jul. 27, 2017 From the US Patent and Trademark Office Re. U.S. Appl. No. 14/658,478. (6 pages).
Notice of Reasons for Rejection dated Sep. 19, 2017 From the Japan Patent Office Re. Application No. 2014-553409. (4 Pages).
Official Action dated Sep. 7, 2017 From the US Patent and Trademark Office Re. U.S. Appl. No. 14/658,478. (37 pages).
Applicant-Initiated Interview Summary dated Nov. 22, 2017 From the US Patent and Trademark Office Re. U.S. Appl. No. 14/658,478. (3 pages).
Notice of Reason for Rejection dated Jan. 26, 2018 From the Japanese Patent Office Re. Application No. 2014-553409 and Its Translation Into English.(5 Pages).
Official Action dated Jan. 12, 2018 From the US Patent and Trademark Office Re. U.S. Appl. No. 14/658,478. (17 pages).
Office Action dated Mar. 15, 2018 From the Israel Patent Office Re. Application No. 233703 and Its Translation Into English. (6 Pages).
Communication Pursuant to Article 94(3) EPC dated Apr. 23, 2018 From the European Patent Office Re. Application No. 13738707.2. (5 Pages).
Notice of Reasons for Rejection dated Sep. 4, 2018 From the Japan Patent Office Re. Application No. 2014-553409 and Its Translation Into English. (4 Pages).
Official Action dated Sep. 21, 2018 From the US Patent and Trademark Office Re. U.S. Appl. No. 14/658,478. (23 pages).

* cited by examiner

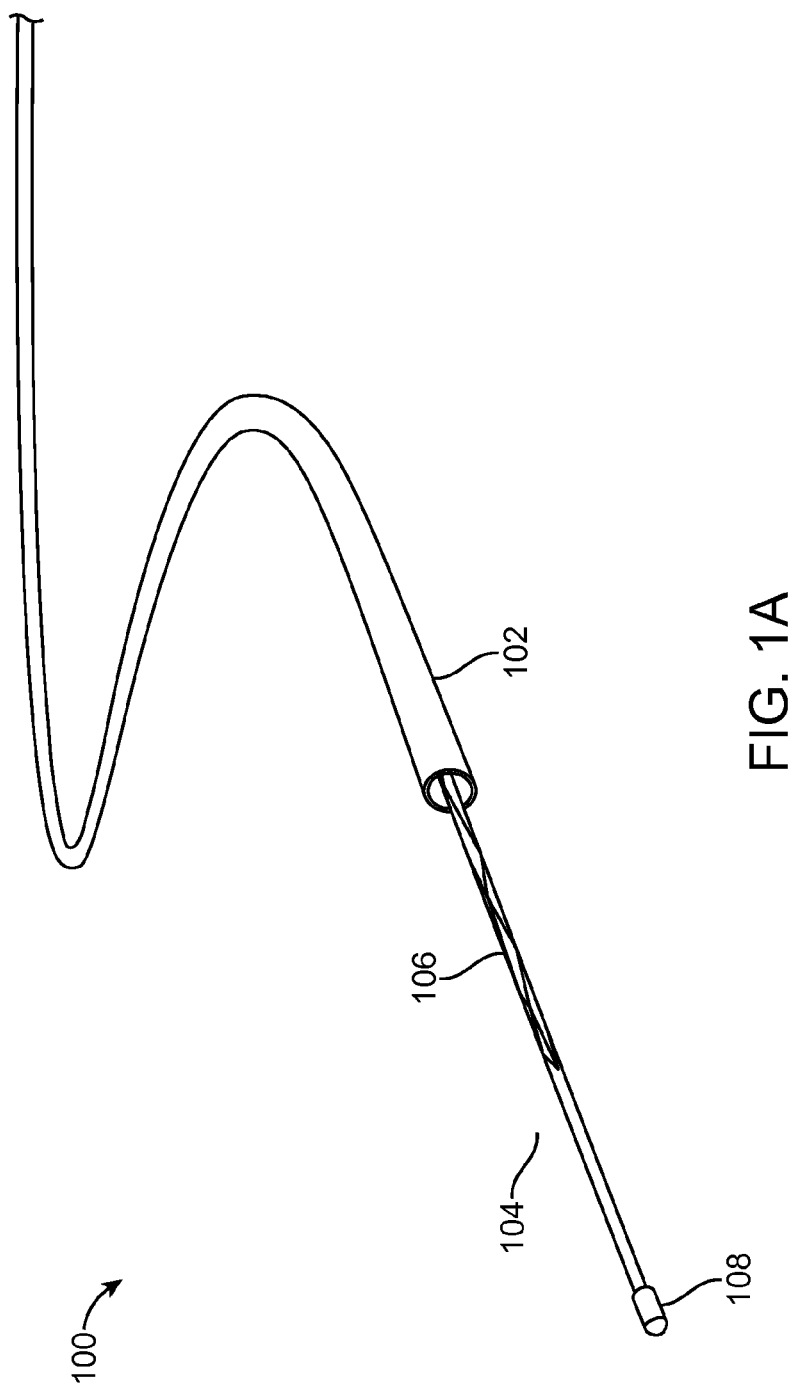

FR=1 where half of the strut is embedded in finite rigidity clot:

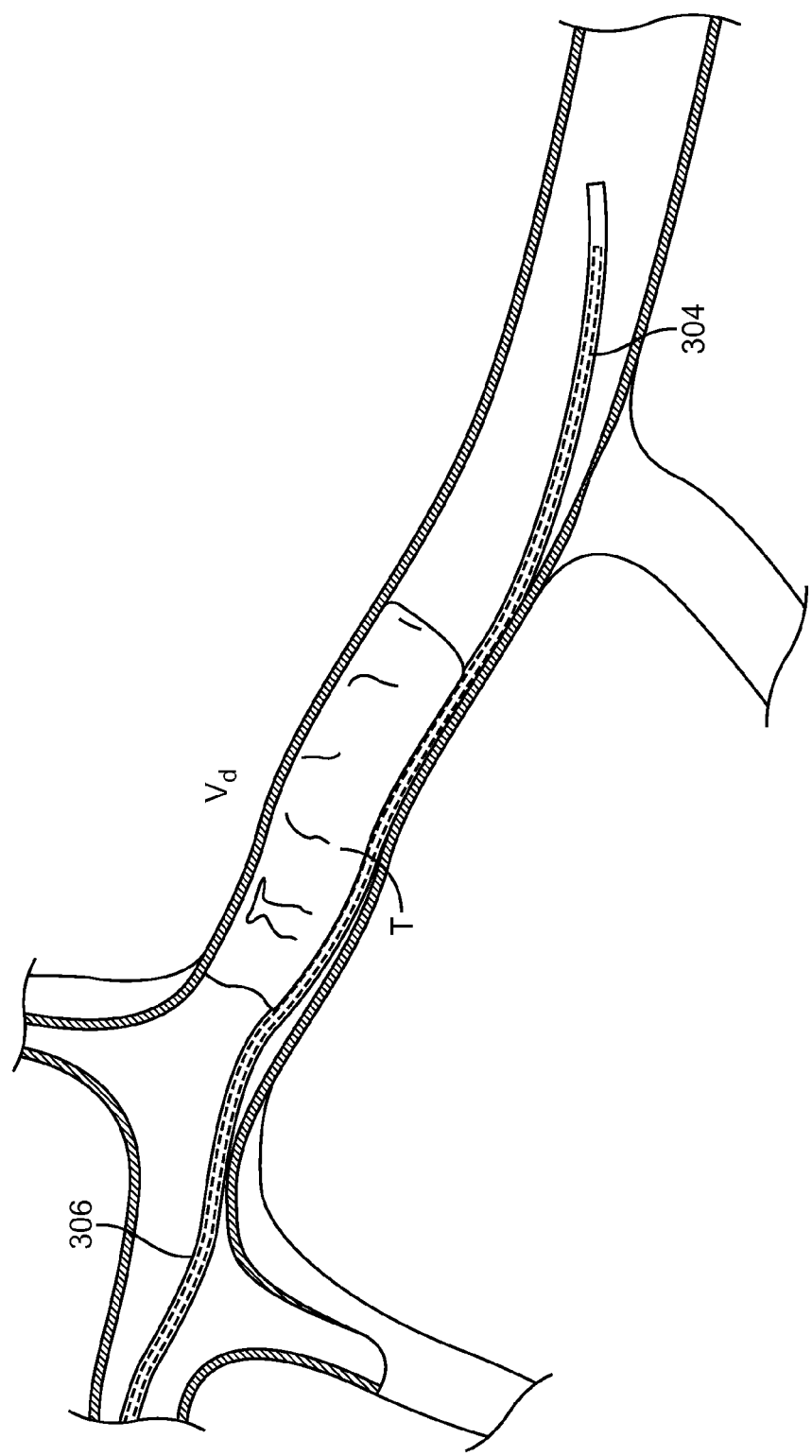

METHOD AND APPARATUS FOR OCCLUSION REMOVAL

CROSS REFERENCE TO RELATED APPLICATION DATA

The present application is a National Phase of PCT Patent Application No. PCT/US2013/021942 having International filing date of Jan. 17, 2013 which is related to and claims the benefit of priority under 35 USC § 119(e) of U.S. Provisional Application Nos. 61/679,508 filed Aug. 3, 2012, 61/693,026 filed Aug. 24, 2012, and 61/587,617 filed Jan. 17, 2012. The contents of the above applications are all incorporated by reference as if fully set forth herein in their entirety for all purposes.

BACKGROUND OF THE INVENTION

Stroke is a leading cause of disability, death and health care expenditure. Most strokes are ischemic (i.e. caused by a decrease in the blood supply to a portion of the brain due to a clot obstructing the flow of blood). A total or hemodynamically significant occlusion of a cerebral artery in an acute ischemic stroke is mostly due to thrombus formation, an embolus, and/or other unwanted matter.

When an artery is obstructed by thrombus, tissue ischemia (i.e. lack of oxygen and nutrients) quickly develops. One therapeutic goal of acute ischemic stroke treatment can be re-establishment of arterial patency, ideally prior to cell death caused by the ischemia. The sooner arterial patency is achieved the greater the clinical benefit, therefore, early restoration of blood flow in the affected territory of the brain may save brain tissue. Drug-based treatments can be used to dissolve the thrombus, but may take hours to take effect.

Fortunately, faster catheter-based thrombectomy treatments exist. Known thrombectomy treatments optionally make use of expandable stent-like devices to drag the occlusion along a blood vessel and into a catheter. One of the most popular devices currently used to perform a catheter based thrombectomy treatment is the Solitaire™ FR Revascularization Device, by ev3 Endovascular, Inc., which has a stent-like expandable cage. The Solitaire™ FR self-expands to a diameter of 4 mm or 6 mm when released, depending on the version selected for use. These self-expanding structures seek to capture the thrombus and may pull at least a portion of the thrombus into a retrieval catheter for removal from the vessel.

While often effective, known thrombus-removal devices, systems, and methods suffer from significant limitations. In particular, expansion forces between self-expanding structures and the vessel wall may vary primarily with the size of the device and the size of the area in which the device is constrained, with the devices often applying forces that increase when the size of the vessel or opening is smaller. Even when the correct size device is initially selected to initially secure the thrombus, the device may not be ideal for moving the thrombus into the retrieval catheter, particularly if the retrieval catheter is positioned at a significant distance from a difficult-to-remove thrombus mass, when the vessel varies in size, has one or more bends, and/or has one or more branches between the thrombus and the retrieval catheter.

BRIEF SUMMARY OF THE INVENTION

Embodiments of the invention provide improved medical devices, systems, and methods. Many of the devices and systems described herein will be beneficial for removal of thrombus from blood vessels, particularly for mitigating neurological damage associated with ischemic stroke. Thrombus associated with ischemic stroke can include a tough, resilient material that can be difficult to break-up, capture within a stent-like cage, or the like. Hence, removal of the material may be facilitated by laterally engaging the material with an expandable member so as to allow the thrombus to be safely pulled into a retrieval catheter. Rather than relying entirely on self-expansion, many embodiments will include expandable members that are configured to controllably expand so as to laterally engage the thrombus with a controlled and variable engagement force. The thrombus may be pulled proximally a significant distance along the vessel from an initial distal position before it can be captured in a retrieval catheter at a proximal position, with the vessel often increasing significantly in diameter, branching, and/or having significant bends between the proximal and distal positions. By allowing a physician to vary thrombus-engagement forces from outside the patient as the thrombus moves, use of the device allows the physician to adjust as appropriate for the changing local conditions along the vessel. Exemplary embodiments of the device include helical and/or braided expandable members coupled with elongate bodies extending proximally from the proximal and distal regions of the expandable members, so that relative movement of the elongate bodies from outside the patient allows controlled actuation of the expandable structure. By providing control over the expansion of the device, the invention may have significant benefits over self-expanding stent-like structures for which expansion forces are dictated by the physical properties of a stent that is only constrained by the thrombus and/or the surrounding vessel.

One embodiment of the invention relates to a method for removing a thrombus. In the method, a catheter can be advanced within a vessel to or past a proximal vessel position. The proximal vessel position is proximal to a thrombus occluding a distal vessel position. An elongate device can be released from the advanced catheter such that an expandable member of the elongate device is in contact with the thrombus. Subsequently, the elongate device can be actuated such that the expandable member expands to a first configuration having a first nominal diameter to apply a first engagement force against the thrombus such that the expandable member axially fixedly engages the thrombus by compression of the thrombus against a vessel wall of the distal vessel position. The elongate device can be retracted while the expandable member remains axially fixedly engaged with the thrombus. This can cause the thrombus to retract from the distal vessel region to an intermediate vessel position between the distal and proximal vessel positions. The intermediate vessel position has a greater diameter than the distal vessel position, and the vessel proximal of the intermediate vessel position may have a greater diameter than the intermediate vessel position such that the first nominal diameter of the expandable member is insufficient in size to maintain axially fixed engagement with the thrombus proximally of the intermediate vessel position. The elongated device can be actuated such that the expandable member expands to a second configuration having a second nominal diameter that is greater than the first nominal diameter to apply a second engagement force against the thrombus such that fixed engagement with the expandable member sufficiently maintained to continue retracting the thrombus proximally of the intermediate position.

Optionally, the device may be used to move the thrombus a significant distance along the vessel wall before the thrombus is captured within a surrounding structure of the catheter system. For example, the device will typically pull the thrombus more than 10 distal vessel diameters, optionally more than 20 diameters, and in some cases more than 50 diameters along the vessel before capture of the thrombus in a lumen of the catheter system.

In some aspects of the method, the catheter can be advanced past the proximal vessel position and at least partially into the thrombus over a pre-positioned guidewire. The guidewire can be subsequently withdrawn while the catheter is maintained in position.

In further aspects of the method, releasing the elongate device includes advancing the elongate device into the catheter such that the expandable member is positioned within the thrombus, and subsequently withdrawing the catheter while the expandable member is maintained in position.

In further aspects of the method, the catheter can be advanced to the proximal vessel position, or past the proximal position and proximal to the thrombus, over a pre-positioned guidewire, and the guidewire can be subsequently withdrawn while the catheter is maintained in position.

In further aspects of the method, releasing the elongate device includes advancing the elongate device into the catheter, such that the expandable member is advanced distally of the catheter, and piercing the thrombus with the expandable member such that at least a portion of the expandable member is positioned within the thrombus. The expandable member can be maintained in an unexpanded configuration before actuating to the first configuration.

In further aspects of the method, the proximal vessel position can have a greater diameter than the intermediate vessel position, such that the second diameter of the expandable member is insufficient in size to maintain axially fixed engagement with the thrombus at the proximal vessel position, and wherein the elongated device is further actuated to expand the expandable member to expand to a third configuration having a third nominal diameter that is greater than the second nominal diameter to apply a third engagement force against the thrombus such that axially fixed engagement with the thrombus is sufficiently maintained to continue retracting the thrombus.

In further aspects of the method, the first engagement force can be less than a desired maximum vessel wall engagement force. The expandable member in the second configuration can be configured so as to, if compressed to the first diameter, exceed the desired maximum engagement force such that delaying articulation of the elongate device from the first configuration to the second configuration till after the elongate device is retracted proximally of the first position inhibits exceeding of the desired maximum engagement force against the vessel wall.

In further aspects of the method, the second engagement force can be equal to or larger than the first engagement force. The intermediate position can have a diameter at least 20% larger than the distal position. In some embodiments, the intermediate position may be at least 30% or even 50% larger than the distal position. The proximal position may have a diameter at least 30% larger than the distal position, often being at least 50% larger than the distal position, and in some cases being more than 100 larger than the distal position.

In further aspects of the method, the intermediate vessel position can include a bend, and optionally a plurality of bends. Articulating of the elongate device from the first configuration to the second configuration can be performed in response to the expandable member being adjacent the bend, so as to inhibit loss of axially fixed engagement of the expandable member with the thrombus being induced by the bend.

In further aspects of the method, the intermediate vessel position can include a branch, optionally a plurality of branches. Articulating of the elongate device from the first configuration to the second configuration can be performed in response to the expandable member being adjacent the branch and so as to inhibit loss of axially fixed engagement of the expandable member with the thrombus being induced by the branch.

In further aspects of the method, the expandable member and the thrombus can be retracted proximally from the vessel into a lumen of a capture catheter, and the elongate device can be activated while retracting the thrombus into the capture catheter in response.

In further aspects of the method, the capture catheter can be affixed within the vessel by expanding a toroidal balloon of the capture catheter. The lumen of the capture catheter may have a diameter at least 10% smaller than that of the proximal position, optionally being at least 20% and in some cases being at least 30% smaller. Actuation of the expandable member may help withdraw the thrombus into the capture catheter.

In further aspects of the method, the expandable member can include a plurality of braided coiled wires configured to assume an expanded relaxed shape when unconstrained.

In further aspects of the method, actuating the elongate device includes pulling a wire coupled to the braided coiled wires such that the braided coiled wires axially compress.

In further aspects of the method, releasing the elongate device includes advancing the elongate device out of the catheter and positioning the expandable member to axially co-occupy the distal vessel position with the thrombus.

In further aspects of the method, the expandable member pierces the thrombus.

In further aspects of the method, the expandable member can be inserted between the thrombus and the vessel wall portion of the distal vessel portion.

In further aspects of the method, the catheter may not be in contact with the thrombus while positioning the expandable member.

In further aspects of the method, the catheter may be of a larger diameter than the diameter of the distal vessel portion.

In further aspects of the method, after piercing the thrombus, the expandable member can be released to radially expand to a relaxed state before being actuated to expand to the first nominal diameter.

In further aspects of the method, in the relaxed state, the expandable member can have a maximum diameter that is less than one half of the diameter of the distal vessel portion.

In further aspects of the method, the elongated device can be actuated a plurality of times while being retracted to the proximal vessel position.

In further aspects of the method, the expandable member can increase in nominal diameter each time for each actuation.

In further aspects of the method, the expandable member can include a plurality of helical wires having a helical diameter that expands to non-uniformly compress the thrombus when applying the first engagement force. Less compressed thrombus portions, between maximally compressed thrombus portions in contact with the wires, can arc inward toward a center axis of the vessel according to a slope angle.

In further aspects of the method, the first engagement force includes a radial force component acting at the maximally compressed thrombus portions. During retraction the wires can further apply an axial force component to the maximally compressed thrombus portions. The radial force component and axial force component together can make up a first moving engagement force.

In further aspects of the method, the radial force component provides a majority of the first moving engagement force.

In further aspects of the method, the second engagement force can maintain or increase the slope angle.

Another embodiment of the invention relates to a catheter system for removing a thrombus from a blood vessel of a patient, the vessel having a proximal vessel position having a proximal vessel diameter and a distal vessel position having a distal vessel diameter with a thrombus occluding the distal vessel position. The system can include microcatheter having a proximal end and a distal end with a lumen therebetween. The lumen can have a lumen diameter and the distal end can be configured for advancement into the vessel beyond the proximal position. The elongate device can have a proximal end and a distal end with an expandable member disposed near the distal end. The distal end can be slidably receivable within the lumen of the microcatheter so that the expandable body is releasable distally from the microcatheter within the vessel. The elongate device can include an actuator disposed near the proximal end. The expandable member can be biased to expand radially from a first configuration to a second configuration when released from the catheter, the second configuration having a nominal diameter larger than the lumen diameter of the microcatheter. The actuator of the elongate device can be operatively coupled to the expandable member and configured so that a first articulation of the actuator from outside the patient expands the expandable member from the second configuration to a third configuration. The third configuration can have a nominal diameter larger than the second configuration to induce the expandable member to apply a first engagement force against the thrombus to axially fixedly engage the expandable member to the thrombus so that withdrawing the expandable member proximally causes the thrombus to retract from the distal vessel region to an intermediate vessel position between the distal and proximal vessel position. The actuator and expandable member can be operatively coupled so that a second actuation of a the elongated device expands the expandable member from the third configuration to a fourth configuration, the fourth configuration having a nominal diameter larger than the third configuration such that the second articulation, when the expandable member is disposed within the vessel in the intermediate position and the intermediate position has a vessel diameter larger than the distal vessel diameter, induces a second engagement force against the thrombus such that fixed engagement with the expandable member is maintained to continue retracting the thrombus proximally of the intermediate position.

Another embodiment of the invention relates to a device for removing a thrombus. The device can be elongated with a proximal end and a distal end. The distal end of the elongate device can be sized to be slidably disposed within a microcatheter. The elongate device can have a distal expandable member adjacent the distal end and a proximal actuator adjacent the proximal end, the actuator functionally coupled to the expandable member. The expandable member can include a non-expanded state, and can be biased to an expanded natural state, and can further be configured to expand by actuation of the actuator to an actuated expanded state larger in profile than the expanded natural state. The expandable member can include a plurality of wires configured to expand to a first nominal diameter that is larger in diameter than the natural state, in order to non-uniformly compress a thrombus within a vessel by application of a first engagement force to form maximally compressed thrombus portions in contact with the wires, and further form less-compressed thrombus portions between the wires that arc inward to a center axis of the vessel according to a slope angle. The expandable member can be further configured to expand to a second diameter that is larger than the first diameter in order to maintain or increase the slope angle.

In some aspects of the system and/or device, the wires can be coiled and interwoven, and configured to expand to approximately ⅓ to ½ of the vessel diameter in the natural state.

In further aspects of the system and/or device, the expandable member can be configured to expand to approximately 6 mm in diameter in a maximally expanded state.

In further aspects of the system and/or device, the wires can be configured to not cut into the thrombus upon expansion, thereby maintaining or increasing the slope angles during expansion of the expandable member.

In further aspects of the system and/or device, the natural state the expandable member can have a continuously curved profile formed between proximal and distal ends.

In further aspects of the system and/or device, a total of 8 wires are interwoven to form the expandable member. Axial distance between the crossed wires longitudinally can be approximately 3.5 mm when the expandable member is expanded to 2 mm in diameter. Axial distance between the crossed wires longitudinally can be approximately 2.4 mm when the expandable member is expanded to 4 mm in diameter.

In further aspects of the system and/or device, a total of 16 wires can be interwoven to form the expandable member. Axial distance between the crossed wires longitudinally can be approximately 1.7 mm when the expandable member is expanded to 2 mm in diameter. Axial distance between the crossed wires longitudinally can be approximately 1.2 mm when the expandable member is expanded to 4 mm in diameter.

In further aspects of the system and/or device, a total of 24 wires can be interwoven to form the expandable member. Axial distance between the crossed wires longitudinally can be approximately 1.1 mm when the expandable member is expanded to 2 mm in diameter, and axial distance between the crossed wires longitudinally can be approximately 0.8 mm when the expandable member is expanded to 4 mm in diameter.

In further aspects of the system and/or device, a pull wire can be moveably coupled between the expandable member and actuator, and configured to expand the expandable member when actuated by the actuator.

In further aspects of the system and/or device, pull wire actuation distance to expandable member diameter ratio ranges from approximately 0.4 at the first diameter to 2.8 at a maximal diameter.

In further aspects of the system and/or device, the first engagement force includes a radial force component acting at the maximally compressed thrombus portions, and wherein during retraction the wires further apply an axial force component, and wherein the radial force component and axial force component together comprise a first moving engagement force.

In further aspects of the system and/or device, a radial force component provides a majority of the first moving engagement force.

Another embodiment of the invention relates to a device for compressing and removing a thrombus to increase blood flow through a vessel. The device comprises an outer tube having a proximal end and a distal end. The tube is sized to be slidably disposed within a microcatheter and the tube has an expandable member adjacent the distal end. A push/pull wire is slidably disposed within the outer tube. The wire has a proximal end and a distal end and the wire is functionally coupled to the expandable member at the distal end. The expandable member is configured to increase diameter from a natural state diameter to a first larger diameter and exert a radial force sufficient to compress the thrombus when an axial force component is applied to the proximal end of the wire by pulling the wire to restore blood flow through the vessel.

In further aspects of the device, the expandable member is configured to decrease diameter from a first larger diameter when an axial force component is applied to the proximal end of the wire by pushing the wire.

In further aspects of the device, the expandable member comprises a plurality of wires configured to divergently compress a thrombus within a vessel by application of a first engagement force to maximally compressed thrombus portions in contact with the wires. The first engagement force comprises the radial force component acting at the maximally compressed thrombus portions. During retraction, the wires further apply an axial force component. The radial force component and axial force component together comprise a first moving engagement force.

In still further aspects of the device, less compressed thrombus portions between the wires arc inward to a center axis of the vessel according to a slope angle during retraction of the device. The expandable member is further configured to expand to a second diameter that is larger than the first diameter in order to maintain or increase the slope angle.

In further aspects of the device, the axial force and the radial force represent a linear relationship with the radial force component comprising a majority of the first moving engagement force.

In further aspects of the device, the axial force and the radial force represent a one-to-one correspondence provided by the equation:

$$Pa = -\frac{2Fc}{DL\tan(\beta)} = \frac{2F}{\pi D^2 \tan^2 \beta}$$

where: Pa=average radial pressure; F=axial force; L=device length; and D=device diameter.

In still additional aspects of the device, the wires are coiled and interwoven, and are configured to expand to approximately ⅓ to ½ of the vessel diameter in the natural state diameter.

In further aspects of the device, the application of the axial force component is provided by a spring, a hydraulic piston, an electromechanic mechanism, or a person.

BRIEF DESCRIPTION OF THE DRAWINGS

FIG. 1A is a perspective partial view of a system and device in an unexpanded configuration, according to embodiments of the invention.

FIGS. 3B-3F are a cross-sectional views of a distal vessel portion illustrating portions of a method for removing a thrombus, according to embodiments of the invention.

DETAILED DESCRIPTION OF THE INVENTION

Figure 1B:
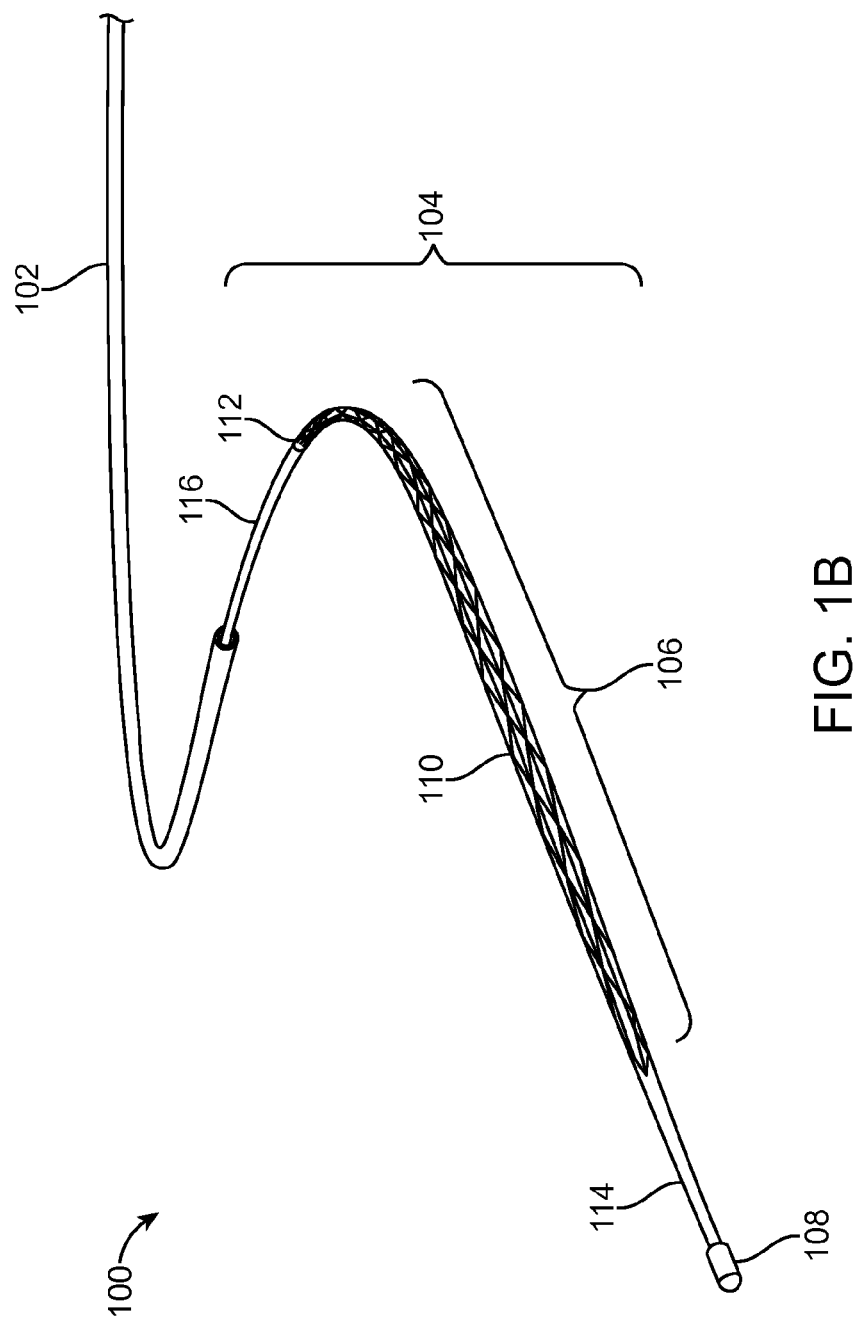
FIG. 1B is a perspective partial view of the system and device of FIG. 1A in a relaxed configuration.

I. Overview:

Embodiments of the invention related to a micro-catheter device having an expandable member. In one embodiment, the expandable member has spirally wrapped (e.g., multiple crossing helixes) and woven filaments in a basket-like configuration. The filaments can be constructed from super-elastic Ni—Ti, with the exception of two filaments constructed from Pt—Ir for radiopacity. In one embodiment sixteen filaments are used, while in another, eight filaments are used.

The proximal ends of the filaments may be connected to a tubular shaft having a small lumen, while the distal ends of the filaments are interconnected to a common joint. A central pull-wire can be connected to the common joint. The pull-wire can be slideable within the small lumen and may be moved relative to the rest of the microcatheter to cause expansion and contraction of the expandable member.

The expandable member can have a relaxed configuration with a diameter in a range from about 1 mm to about 3 mm, optionally being a 2 mm diameter. When housed within and moving axially along the microcatheter, the expandable member is configured to be compressed to 1 mm or less. In one embodiment, the expandable member can expand beyond the relaxed size via manipulation of the pull-wire to expand to up to 4 mm. Relative proximal movement of the pull-wire causes the expandable member to expand, while distal movement causes contraction.

For small vessels, a capture catheter may be positioned proximately from the occlusion, with the proximal region surrounding the capture catheter typically having a significantly larger diameter than that of the vessel surrounding distal thrombus. For example, when the thrombus is located in a distal region having a 2 mm to 4 mm diameter, the capture catheter may be located in a region having a vessel diameter of 5 mm or more. Upon retraction of the expandable device and the engaged thrombus from the smaller vessel to the larger vessel, absent any control over the expansion of a self-expanding device the expansion force applied by such a self-expanding device against the surrounding vessel wall (and against the thrombus) would decrease, so that the device might fail to maintain adequate force to keep hold of the thrombus, risking loss. Moving the expanded device with the thrombus around vessel corners may also be problematic, particularly should a stent-like self-expanding device kink to some degree, and thus apply less expansive force to the thrombus, again, risking loss of axial control over the thrombus.

In use, the device can be placed within an occlusion while the device is constrained within the microcatheter. The device can then be released to the relaxed state by withdrawing the surrounding catheter sheath, and further expanded within the occlusion by relative proximal movement of the pull-wire to affect expansion, so as to axially secure the device to the thrombus thereby a first force is applied. Once the thrombus is secured to the device (typically with most or all of the thrombus remaining outside the expandable device), the thrombus may be withdrawn along the vessel wall by retracting the device, the device and thrombus often being pulled along the lumen for a considerable distance while the lumen gradually increases in diameter. Once the thrombus and device have been pulled into a sufficiently larger region of the vessel, the device and thrombus are pulled into and captured by a capture catheter.

As the occlusion is moved proximally from its original position, vessel diameter generally increases. As a result, the force being applied to the captured occlusion could become inadequate if no adjustments in the device were made (e.g. during a limited portion of the overall movement, analogous to the prior methods). A surgeon can counteract this by causing relative proximal movement of the pull-wire to affect expansion of the expandable member, thus applying an increased or second axial force to the pull-wire, causing a corresponding increased or second radial force to be applied by the device to the surrounding thrombus and vessel wall. Accordingly, the expandable member may maintain a substantially constant or increasing amount of pressure against the occlusion as it axially moves away from the axis of the expandable member.

Thus, in one example, the inventive expandable member applies a first force by actuation of the pull-wire to overcome the expandable member's resilient nature to maintain its natural shape and the compressive forces applied by the thrombus. The expandable member applies a second force by actuation of the pull-wire, to maintain or exceed the pressure applied to the thrombus. When the radial reactive force decreases due to a larger surrounding vessel lumen, further actuation of the pull-wire can again apply further force if necessary. Thus, pressure against the occlusion can be increased or maintained as the size of the vessel wall increases in size.

II. Exemplary System and Device:

FIG. 1A shows a system 100 for removing obstructions from a body passage, such as a thrombus from a small blood vessel. The system 100 includes a catheter 102, which may be a microcatheter (i.e. diameter of 5-French or less) for use in small vessels (2 mm to 4 mm), typically intracranial blood vessels. The catheter 102 can be constructed from hollow tubing, such as a flexible polymer (e.g., polyether-block-amide, commercially available under the name PEBAX from the ARKEMA GROUP of Paris, France) tubular extrusion. In some embodiments, the catheter 102 can be reinforced with braiding and configured for withstanding high pressure for delivering liquid medication. The catheter 102 is generally configured for use over a guidewire, but may additionally include provisions for steering. The catheter 102 can also include radio-opaque elements to aid fluoroscopic visualization.

The system 100 further includes an elongate device 104, which is configured to slide within the catheter 102. The elongate device 104 includes an expandable member 106, which is shown in FIG. 1A in a constrained or unexpanded position. In the unexpanded configuration the expandable member can have a diameter of 1 mm, which is typically half the size of the smallest diameter vessels encountered during use. In some embodiments, the expandable member 106 can be controllably restrained at a proximal end (not shown) of the elongate device 104, while in other embodiments the expandable member 106 can be constrained by the inner diametrical constraints of the catheter 102. The distal end 108 of the elongate device 104 can be constructed from radio-opaque material (e.g. in the form of a cap) to aid fluoroscopic visualization, and generally the elongate device can include a plurality of embedded radiopaque makers.

FIG. 1B shows the expandable member 106 advanced distally from the catheter 102. The expandable member 106 can be constructed from a plurality of wires 110. Each wire 110 is formed as a coil having a substantially cylindrical or curved profile that tapers to a point at each of its ends. The distal end of wire 110 tapers to its end on the distal end 108. The proximal end of wire 110 tapers to its end on the proximal end 112. The wires 110 are interwoven with one another so as to form a braided basket-like structure. The wires 110 are also moveable with respect to one another between the proximal end 112 and distal end 108.

Relative axial displacement of a pull-wire 114, which is fixed to the distal end 108 but not the proximal end 112, with respect to a tube 116 of the elongate device 104 causes the expandable member 106 to expand or contract, depending on the relative movement of the pull-wire 114. In this embodiment, relative distal movement of the pull-wire 114 causes the expandable member to elongate axially and thus contract, to resemble the state shown in FIG. 1A. In the contracted state, the expandable member can have a diameter of approximately 1 mm. Likewise, relative proximal movement of the pull-wire 114 causes the expandable member to compress axially and thus expand.

The wires of the expandable member 106 can be constructed from a resilient material, such as nickel-titanium alloy or stainless steel, or a mixture of different metals (e.g. 15 NI—Ti wires and 1 Platinum), since Platinum wire is relatively easier to see under fluoroscopy. The wires 110 can be coated to increase lubricity or enhance fluoroscopic visualization. In some embodiments, 16 wires are used, while in other embodiments 8 wires can be used. Each wire can have a diameter of 0.005 mm.

The wires 110 can be formed from a substantially elastic or super elastic alloy and configured to assume a relaxed state (i.e. with the pull-wire 114 applying force to the distal end 108) as shown in FIG. 1B. The wires 110 can be round in cross-section or have distinct orthogonal sides (e.g. rectangular). In some embodiments the wires 110 are formed as individual micro-coils. In the relaxed stated, the expandable member 106 can have a nominal (i.e. without external constraint) diameter of 1.5 mm.

Figure 1C:
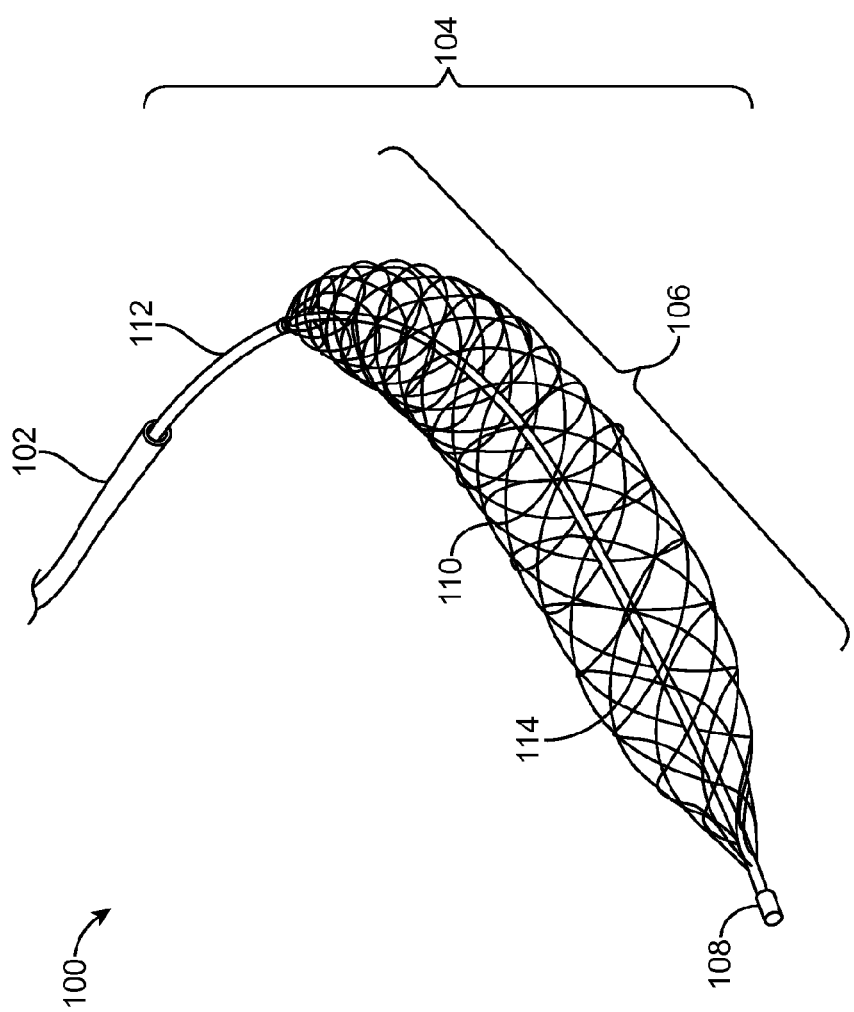
FIG. 1C is a perspective partial view of the system and device of FIG. 1A in an expanded configuration.

FIG. 1C shows the expanded state of the expandable member 106. In the expanded stated, the expandable member 106 can have a nominal diameter of 4 mm. The actuator 100 is shown in a curved configuration to illustrate flexibility, however, it generally assumes a straight shape, although in some embodiments the elongate device 104 can have a resiliently bent or curved distal end (e.g. 45 degrees) to help enable access to certain veins.

Figure 2A:
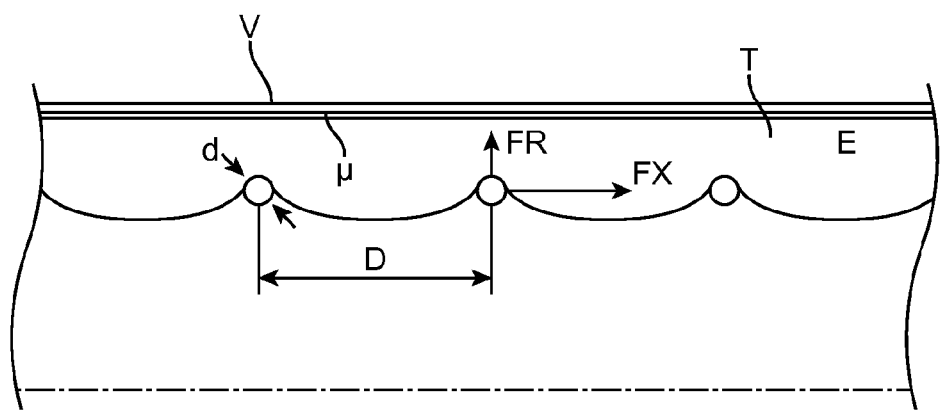
FIGS. 2A-2C are simplified diagrams illustrating forces involved in removing a thrombus using an expandable member, according to an embodiment of the invention.

III. Force Diagrams:

FIG. 2A shows the expandable member 106 in use. A portion the expandable member 106 is shown in cross-section within a half-section of a vessel. The wires 110 are shown "squeezing" a thrombus T (having a modulus of elasticity E), against a vessel wall V. The wires 110 generally do not cut the thrombus, but compress it along an axis through the thrombus created by the catheter 102 in conjunction with a guidewire, or by dissection of the thrombus using the elongated device 104 alone. The wires 110 are arranged such that they are separated by a distance D at a certain expanded diameter of the expandable member 106. Nominal distances corresponding to nominal diameters of the expandable member 106 are shown below in TABLE 1.

TABLE 1

| Nominal Outer Diameter (mm) | Nominal axial distance between wires D (mm) | |
| --- | --- | --- |
| | 8 wires | 16 wires |
| 4.00 | 2.43 | 1.18 |
| 3.80 | 2.61 | 1.26 |
| 3.60 | 2.76 | 1.34 |
| 3.40 | 2.90 | 1.41 |
| 3.20 | 3.02 | 1.46 |
| 3.00 | 3.13 | 1.51 |
| 2.80 | 3.23 | 1.56 |
| 2.60 | 3.31 | 1.60 |
| 2.40 | 3.39 | 1.63 |
| 2.20 | 3.45 | 1.65 |
| 2.00 | 3.50 | 1.67 |

There is a limited envelope of relations between the physical properties of the thrombus T and vessel wall (e.g. modulus E, Coefficient of friction $\mu$, etc.) and the geometrical values of the expandable member 106 (d, D, etc.), that create the conditions in which the interaction between the expandable member 106 and the thrombus T enables removal of the thrombus. In the relaxed state, as shown in FIG. 1B, the expandable member 106 will apply a certain amount radial force FR against the thrombus. Additionally, the pull-wire 112 can be moved proximately, relative to tube 116, to increase or add additional radial force by applying a certain amount of axial force to the pull-wire. Accordingly, more radial force FR can be applied to fixedly engage the expandable member 106 to the thrombus T, so both will slide within the vessel.

Since the artery size is not constant (e.g. enlarges towards the proximal direction), the radial FR force can be increased or maintained by applying additional longitudinal force to the pull-wire 110 incrementally, and thus maintain the envelope of parameters that enable engagement of the thrombus T and avoid relative sliding between the expandable member 106 and the thrombus T. TABLE 2 below shows one inventive example of a device made from sixteen 0.05 mm diameter Ni—Ti wires. The device self expanding force expand the device to 1.5 mm and the expansion to any larger diameter is made by pulling the wire.

TABLE 2

| Device diameter due to wire pulling [mm] | Radial pressure applied to thrombus/artery wall [Pa] | Force applied to the pull-wire [N] | Relative length the wire is pulled [mm] |
| --- | --- | --- | --- |
| 4 | 1681 | 0.036 | 11.34 |
| 3.75 | 1377 | 0.034 | 9.21 |
| 3.5 | 1137 | 0.031 | 7.35 |
| 3.25 | 935 | 0.028 | 5.71 |
| 3 | 753 | 0.024 | 4.26 |
| 2.75 | 580 | 0.020 | 2.98 |
| 2.5 | 404 | 0.015 | 1.85 |
| 2.25 | 215 | 0.008 | 0.86 |
| 2 | — | — | — |

Prior self-expandable devices may be designed to create thrombus removal conditions, but since the vessel becomes bigger towards its proximal side, the predefined radial force will not necessarily maintain the required engagement conditions, thus risking loss of the thrombus T.

Figure 2B:
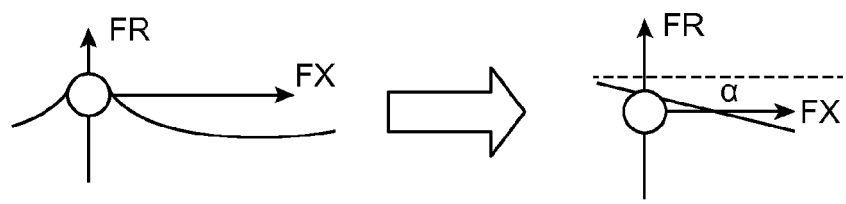

FIG. 2B illustrates a simplified interaction of radial force FR and frictional force FX between the wires 110 and the thrombus T. As shown, the expandable member 106 non-uniformly compresses the thrombus when applying radial force FR. Thus, portions between the wires 110 are comparatively less compressed than portions of the thrombus in contact with the wires. The less compressed portions are inward to a center axis of the vessel, which can be simplified to a slope angle $\alpha$. Thus, slope angle $\alpha$ represents the degree of wire 110 to the thrombus engagement, i.e., the greater slope angle $\alpha$ the greater the engagement. Slope angle $\alpha$ is dependent on the modulus of elasticity E and radial force FR.

Figure 2C:
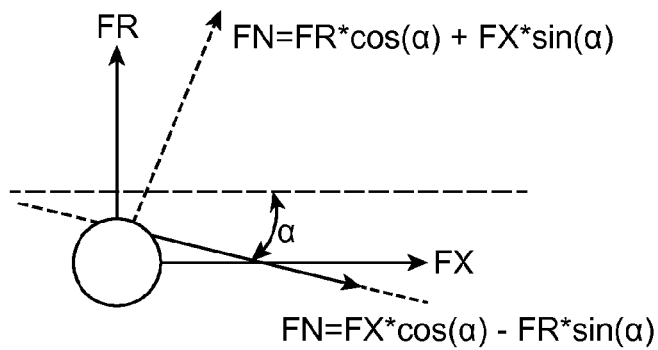
Figure 2D:
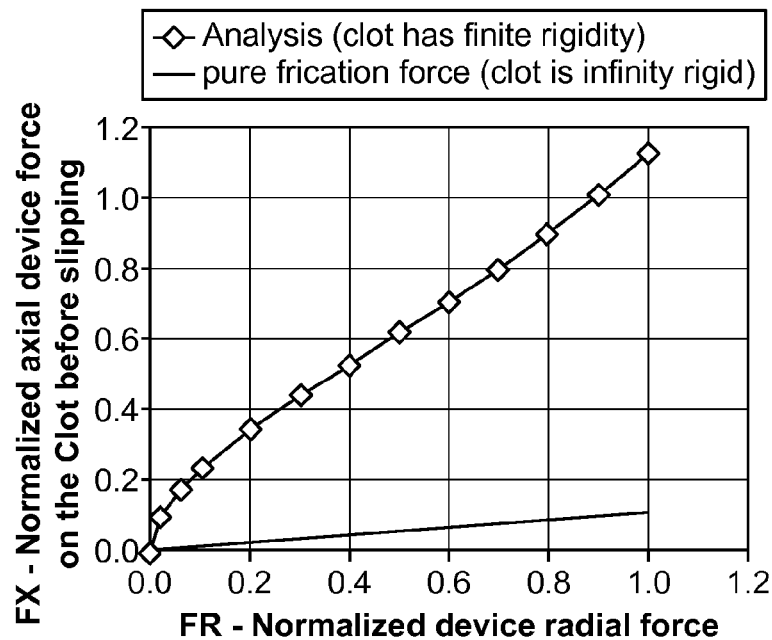
FIG. 2D is a graph of force values for removing a thrombus using an expandable member, according to an embodiment of the invention.
Figure 2E:
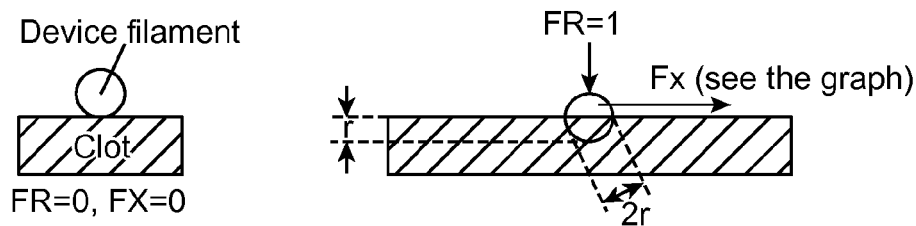
FIG. 2E is a simplified diagram illustrating forces involved in removing a thrombus using an expandable member, according to an embodiment of the invention.

FIG. 2C shows a model interaction of force components using slope angle $\alpha$ represent the clot elasticity. Axial force is applied to the actuator 100 create radial force FR. The axial force FX to move (retract) the clot is connected to the radial force FR. Static friction force calculated as $FT=FN*\mu$, where $\mu$ is constant. Using the calculation above and the relation between FN/FT to FX/FR with simple trigonometry can be calculated and presented in the FIGS. 2D and 2E. The graph represents two lines. One is for a non elastic clot; the axial force one can generate is low. The second is for an elastic clot and with a use of high radial force such as can be generated by applying actuator 100. The axial force to move the clot due to friction is much higher.

Figure 3A:
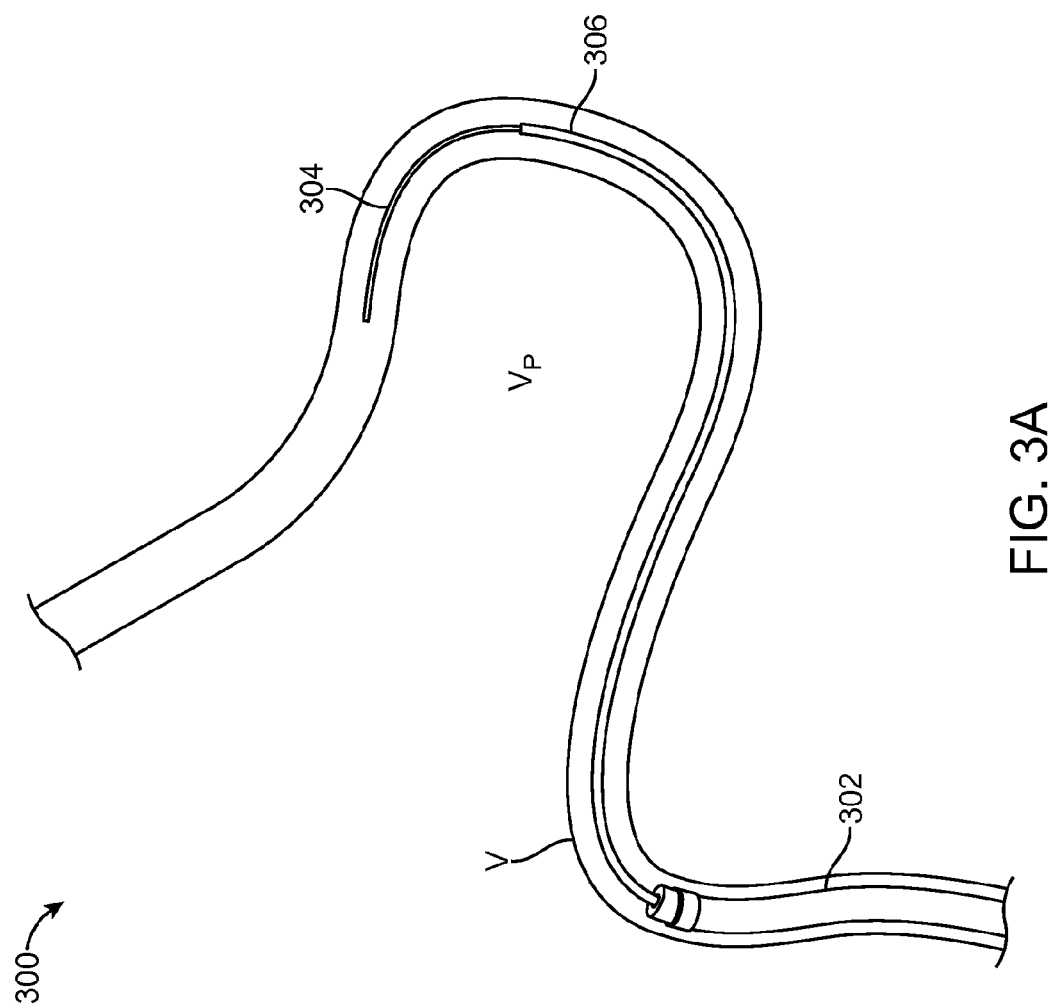
FIG. 3A is a cross-sectional view of a proximal vessel portion illustrating a portion of a method for removing a thrombus, according to an embodiment of the invention.

IV. Exemplary Method:

FIG. 3A illustrates a portion of a method 300 for removing a thrombus using the device of FIG. 1A. A capture catheter 302 is shown introduced into a vessel V, which can be performed under fluoroscopic guidance using a guidewire 304. The vessel V may be a intracranial vessel. The capture catheter 302 can be maintained at or proximally to a proximal vessel portion $V_p$ of the vessel V, or to a portion where it can advance no further due to decreasing vessel diameter and/or torturous vessel anatomy. A microcatheter 306, which corresponds to catheter 102 of FIG. 1A is advanced, over the guidewire 304 and then advanced distally beyond the capture catheter 302.

Figure 3B:
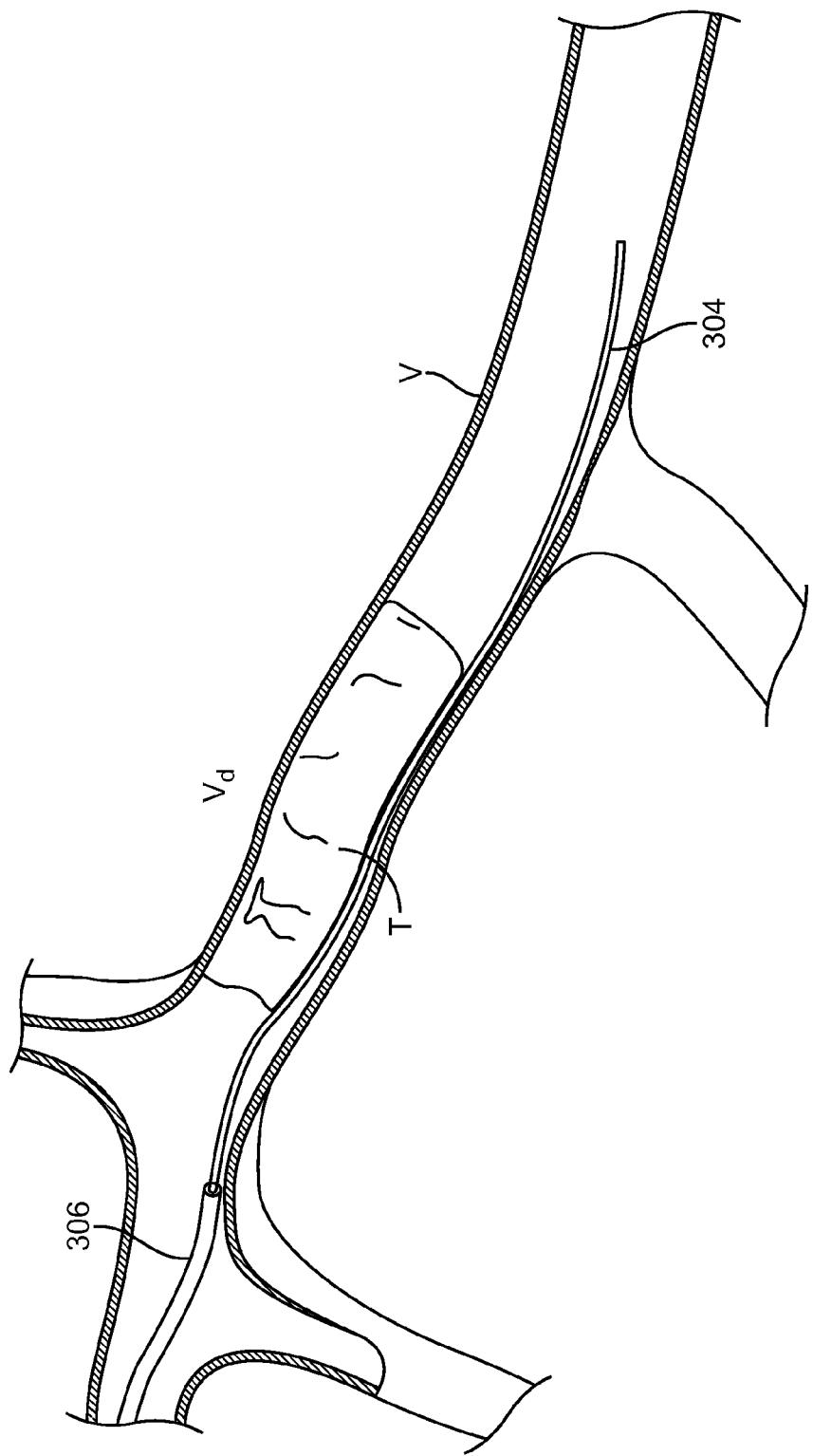

FIG. 3B illustrates yet another portion of the method 300. As shown the microcatheter 306 and guidewire 304 have been advanced past the proximal vessel portion $V_p$ to a distal vessel portion $V_d$ of the vessel V (or a branch thereof) where a thrombus T is located. The distal vessel portion $V_d$ may roughly have a diameter of 2 mm to 5 mm. The guidewire 304 is axially advanced through the thrombus T to rest at a position distal to the thrombus T. In practice, the guidewire 304 may pierce the thrombus throughout, and/or slide between the thrombus T and the vessel wall.

FIG. 3C illustrates yet another portion of the method 300. While the guidewire 304 is maintained in position, and the microcatheter 306 is over the guidewire 304 such that at least a portion of the microcatheter 306 is within the thrombus T. As shown, a distal portion of the microcatheter 306 is well advanced beyond the thrombus T, but this is not necessarily required for performing the method 300.

Figure 3D:
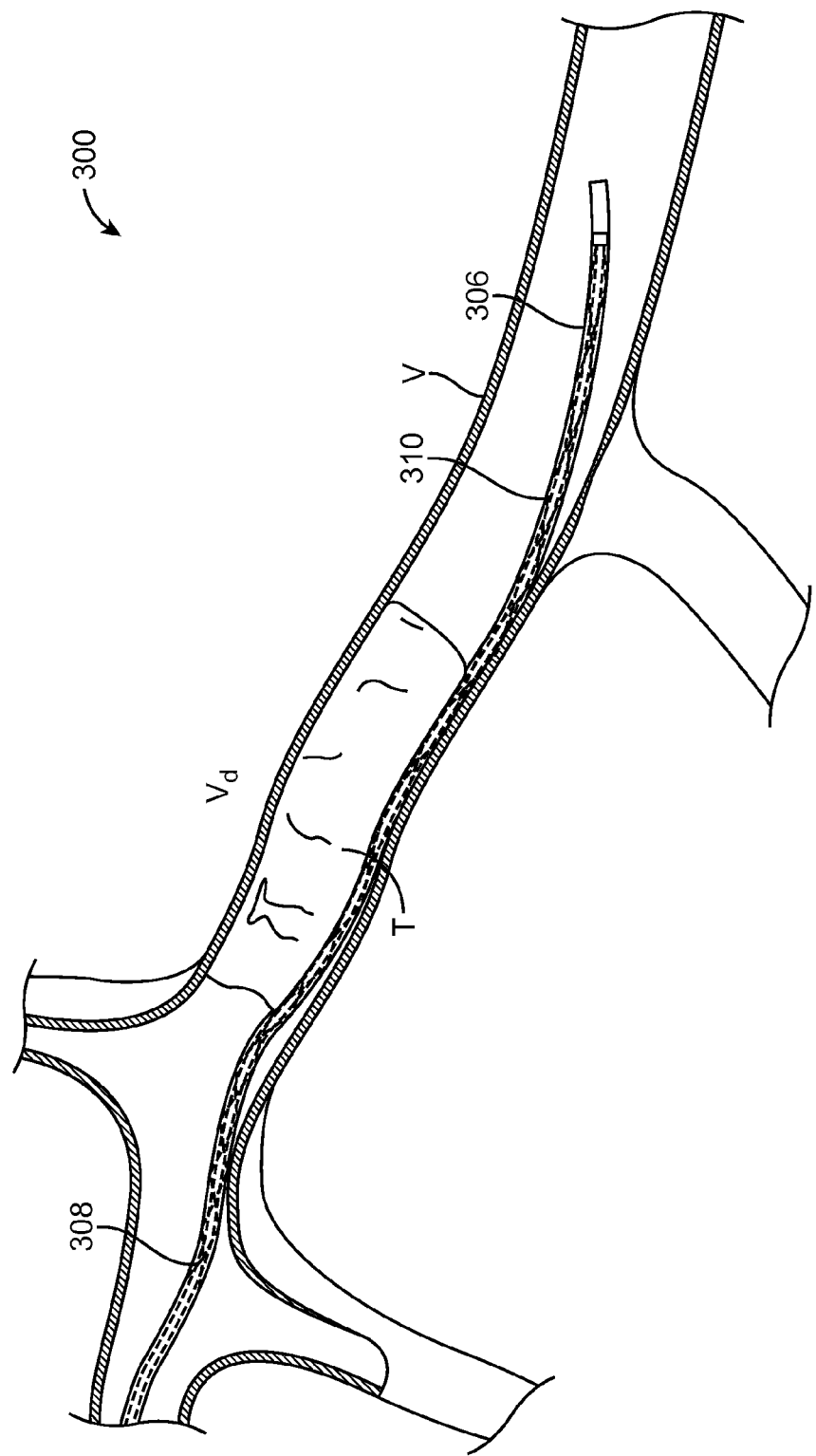

FIG. 3D illustrates yet another portion of the method 300. The guidewire 304 is withdrawn and removed from the microcatheter 306, leaving an interior lumen of the microcatheter 306 vacant. An elongate device 308 is subsequently advanced within the interior lumen of the microcatheter 306 while the position of the microcatheter 306 is maintained. The elongate device 308 is advanced until a expandable member 310 is at least partially within or adjacent to the thrombus T, such that the expandable member 310 coaxially occupies the same vessel location as the thrombus T and separated from contact with the thrombus T by the microcatheter 306. As shown, a distal portion of the expandable member 310 is advanced well beyond the thrombus T, but this is not necessarily required for performing the method 300.

Figure 3E:
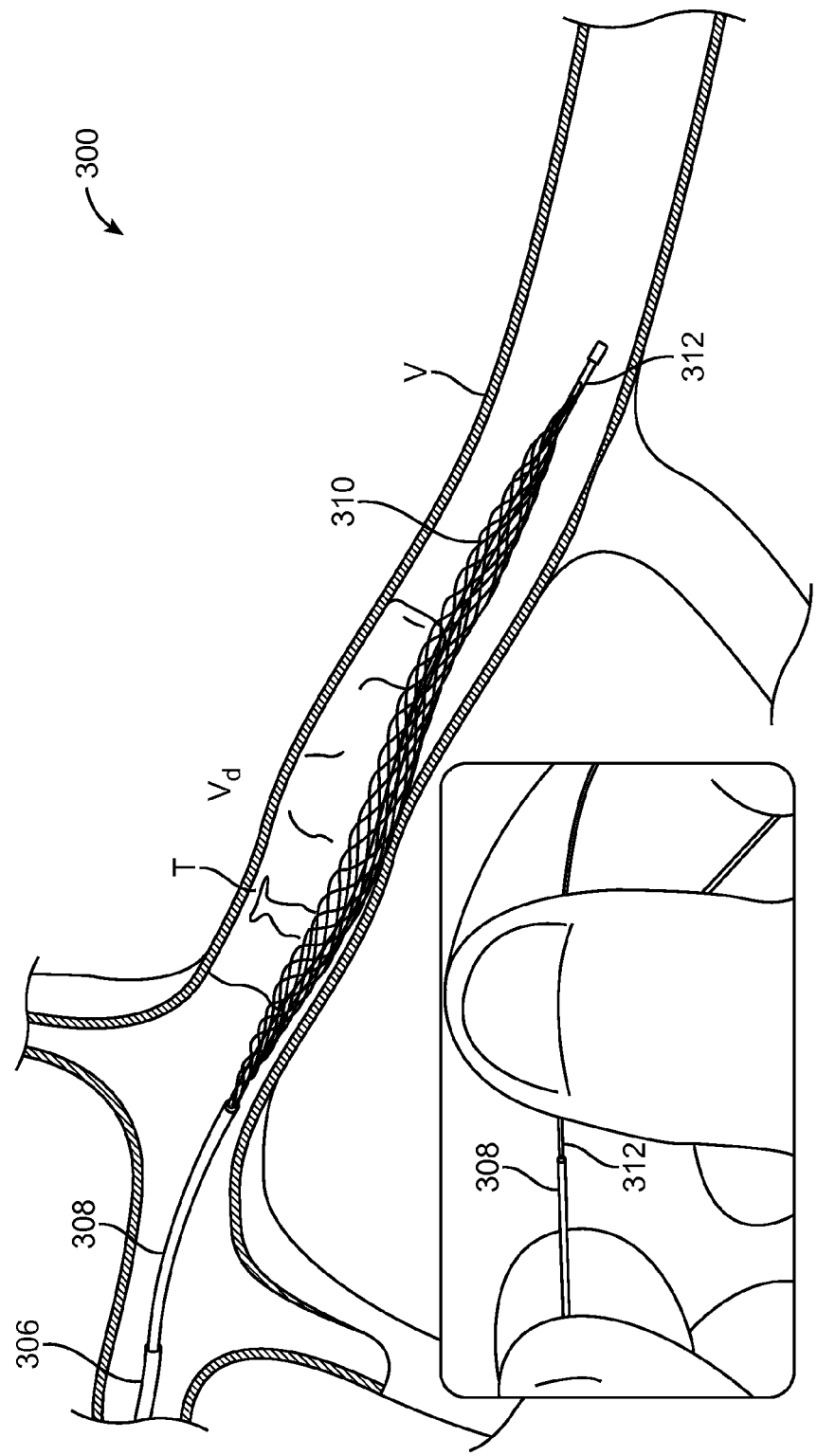

FIG. 3E illustrates yet another portion of the method 300. Here, the microcatheter 306 is withdrawn such that it is proximal to the thrombus T, while the position of the elongate device 308 is maintained. This causes the expandable member 310 to come into contact with the thrombus T and expand from a contracted position to a relaxed configuration. Expansion may occur by simply removing the microcatheter 306, which can physically constrain the expandable member 310. Alternatively, a proximal end of a pull-wire 312 can be released from a locked configuration (relative to the main structure of the elongate device 308) to a free configuration. This may occur from breaking a simple proximal bond between the proximal end of the pull-wire 312 and another portion of the elongate device or by triggering a handle mechanism.

Figure 3F:
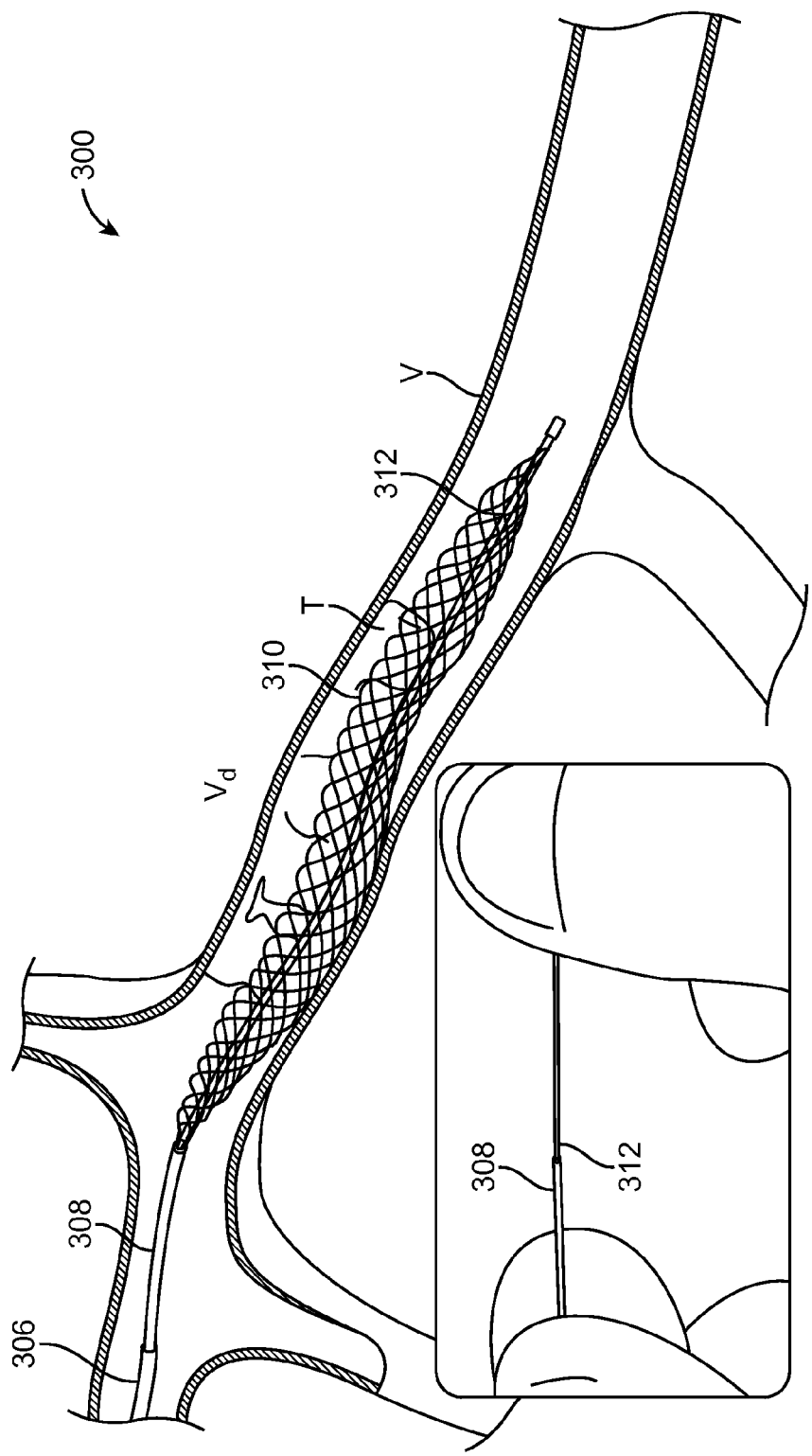

FIG. 3F illustrates yet another portion of the method 300. Here, the pull-wire 312 is proximately displaced in an axial direction, relative to the elongate device 308. This causes the expandable member 310 to axially contrast and diametrically expand from the relaxed configuration shown in FIG. 3E to a first expanded configuration. The actual expanded diameter of the expandable member 310 is dictated by many factors, but namely the degree of physical constraint enacted by the thrombus T and vessel walls, and the amount of force applied to the pull-wire 312. For the purposes of practicing the method 300, generally, the actual expanded diameter can be less than or equal to a nominal expanded diameter (i.e. a particular diameter for which no constraint is applied to the expandable member 310 while a particular force is applied to the pull-wire 312). Accordingly, a particular distance (and/or force) that the pull-wire 312 is displacing can be correlated to a particular nominal diameter.

The expandable member 310 is shown expanded to a first configuration that correlates to a first nominal diameter. The first configuration is determined by the amount of force applied to the pull-wire 312. In the first configuration wires of the expandable member 310 apply an engagement force sufficient enough to maintain engagement with the thrombus T during axial displacement. Put another way, the engagement force is the minimum force required to prevent the thrombus T from sliding off the wires during withdrawal. The wires of the expandable member 310 generally do not cut into the thrombus T, rather, the wires compress the thrombus T against the vessel wall. The more compressed the thrombus T is, the greater a correlated slope angle between the wires and the thrombus (as shown in FIG. 2B), thus providing a greater axial surface area to pull against as the slope moves to vertical. However, this also applies greater pressure between the thrombus T and the vessel wall. Accordingly, the engagement force must be sufficient enough to overcome frictional force between the thrombus T and the vessel wall.

Perhaps ideally, the engagement force would correspond to a desired maximum value when initially applied to the thrombus T, this maximum value being great enough to maintain fixable engagement with the thrombus T for the entirety of the procedure. Put another way, it would be ideal to simply once apply a first engagement force that is great enough to overcome all predictable vessel size and geometries changes as the thrombus T is dragged back to the capture catheter 302. However, in practice, such a maximum force can be great enough to overstress the vessel at the distal vessel portion $V_d$. Thus, the initial engagement force may be lower than a desired maximum force, yet great enough to initially dislodge the thrombus T and move it a particular distance to a different portion of the vessel V where the maximum engagement force can be applied in a safe manner.

Figure 3G:
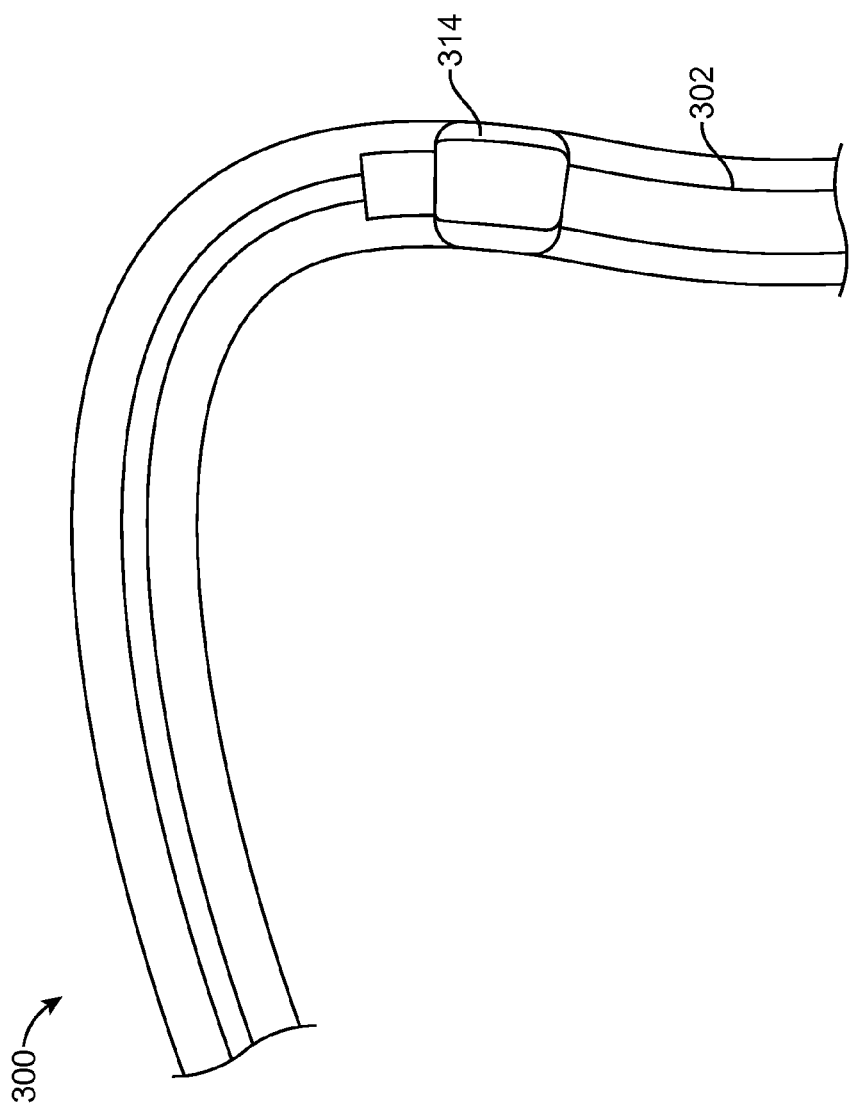
FIG. 3G is a cross-sectional view of a proximal vessel portion illustrating a portion of a method for removing a thrombus, according to an embodiment of the invention.

FIG. 3G illustrates yet another portion of the method 300. Here, a balloon 314 of the capture catheter 302 is inflated to halt blood flow. In some cases this can ease withdrawal of the thrombus T. However, stopping blood flow is optional and not required to practice the method 300.

Figure 3H:
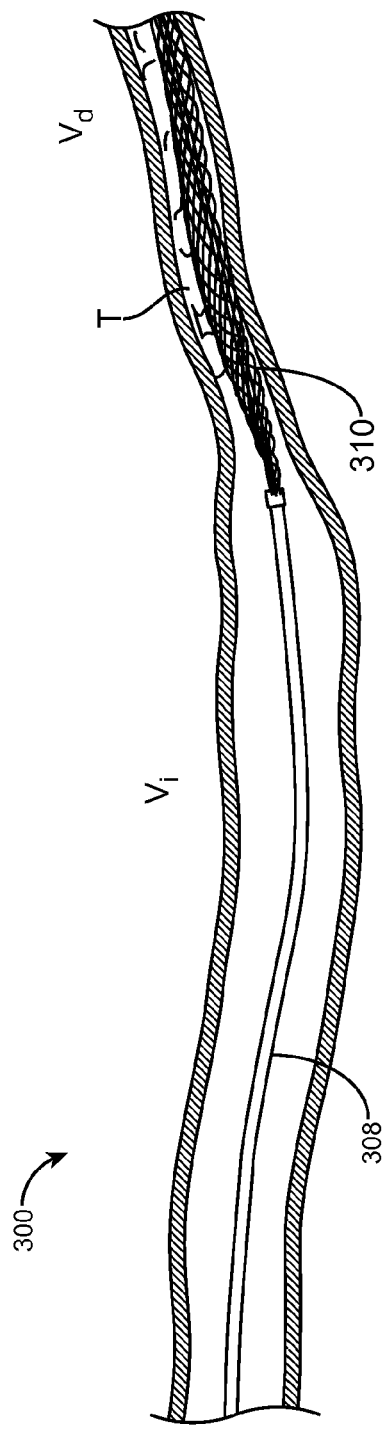
FIGS. 3H and 3I are a cross-sectional views of an intermediate vessel portion illustrating portions of a method for removing a thrombus, according to embodiments of the invention.

FIG. 3H illustrates yet another portion of the method 300. Here, the thrombus T is being withdrawn proximally within the vessel V, from the distal vessel portion $V_d$ to an intermediate vessel portion $V_i$, which is distal of the proximate vessel portion $V_p$. As shown, vessel diameter at the intermediate vessel portion V, is larger than the vessel diameter at the distal vessel portion $V_d$. The difference is great enough such that the first engagement force of the expandable member 310 will no longer be sufficient to maintain fixable engagement with the thrombus T. Accordingly, correlated slope angle between the wires and the thrombus (as shown in FIG. 2B) will move to horizontal. The method 300, however, compensates for the change in vessel diameter.

Figure 3I:
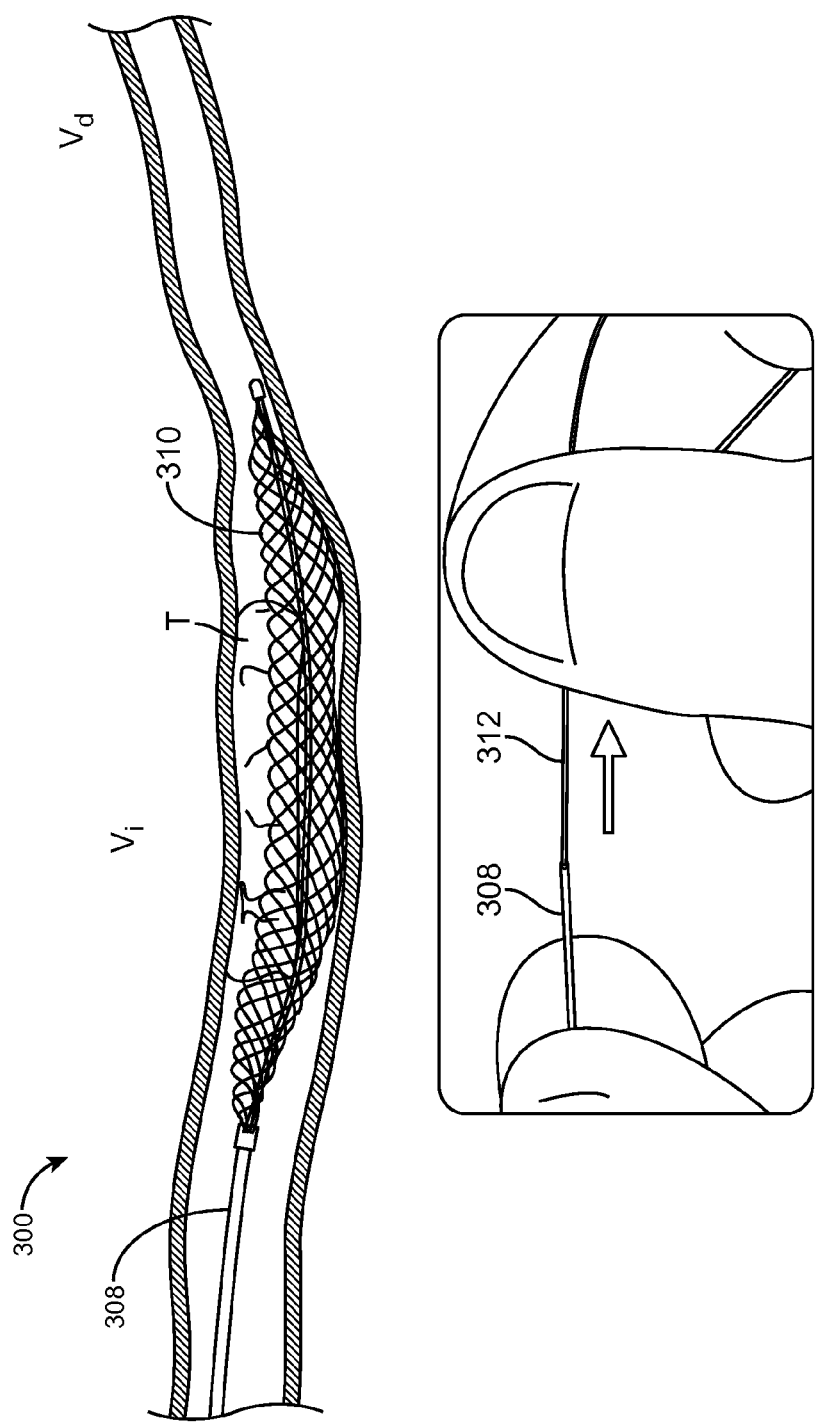

FIG. 3I illustrates yet another portion of the method 300. Here, the pull-wire 312 is actuated further at the intermediate vessel portion V, to a second expanded configuration that correlates to a second nominal diameter, which is greater than the first nominal diameter of the first expanded configuration. The increase in vessel diameter at the intermediate vessel portion V, can be greater than 20% as compared to the distal vessel portion $V_d$, and in some cases greater than 100%. In the second expanded configuration, a second engagement force is applied to the thrombus to maintain fixed engagement under axial movement. The second engagement force is typically, but not necessarily, greater than the first engagement force, and in some cases is equal.

The intermediate vessel portion V, is shown as a diametrically larger vessel portion, as compared to the distal vessel portion $V_d$, however, this is not necessarily the case. The increase in diameter can be an effective increase rather than an actual one. For example, in the case of encountering a vessel branch or a sharp vessel direction change, the expandable member 310 may have the tendency to straighten rather than conformingly bend with the vessel. Thus, portions of the expandable member may compress or kink enough to render the first engagement force insufficient to maintain axially fixed engagement. Accordingly, the expandable member 310 can be further actuated to compensate for such changes.

It should be understood that further changes in the expanded configuration of the expandable member 310 are possible as the thrombus T is withdrawn. For example, at the proximal vessel portion $V_p$, the expandable member 310 can be actuated to a third expanded configuration can that correlates to a third nominal diameter, which is greater than the second nominal diameter of the second expanded configuration. In this third configuration a third engagement force is applied to the thrombus, such that axially fixed engagement is maintained.

It should be further understood that the changes in expanded configurations as illustrated above are incremental only to ease understanding of the method 300. In some embodiments, a gradual force change can be applied to the pull-wire 312. In some embodiments, this change can be actuated manually by a user directly manipulating the pull-wire 312, as shown in FIG. 3I, or by using an actuator. Such an actuator may, for example, be a ratcheting wheel that provides a mechanical advantage. An example of such an actuator is shown in U.S. Pat. No. 7,198,635, which is incorporated herein by reference. As shown in Table 2, pull wire actuation distance to expandable member diameter ratio can range from approximately 0.4 to 2.8. Thus, pull-wire actuation at the larger diameters is relatively small. The actuator can be configured to use a geared configuration such that applied distance to pull wire actuation distance ratio is greater than 1, such as 2:1 or 4:1 (e.g., 4 mm of input causes 1 mm of pull-wire retraction). Thus, actuation of the pull-wire at the larger diameters can be performed in a very tactile manner.

Figure 3J:
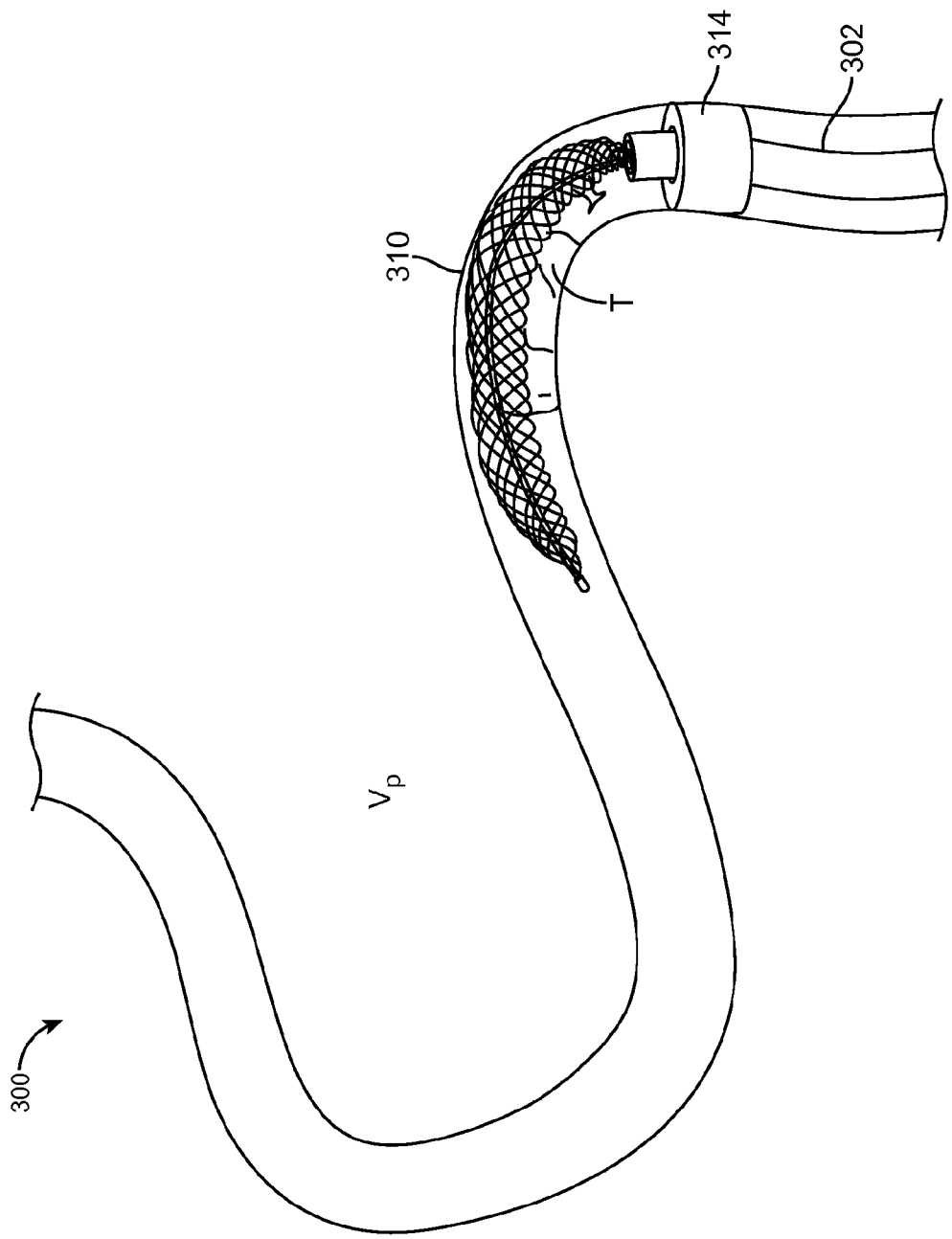
FIG. 3J is a cross-sectional view of a proximal vessel portion illustrating a portion of a method for removing a thrombus, according to an embodiment of the invention.

FIG. 3J illustrates yet another portion of the method 300. Here, the expandable member 310 and thrombus T are withdrawn into a lumen of the capture catheter 302. During this process, the expandable member 310 can be actuated to reduce the expanded diameter of the expandable member in order to enable retraction into the lumen. This may occur during retraction in order to prevent loss of the thrombus T. If provided, the inflatable balloon 314 can be deflated after the retraction of the thrombus T is complete, to restore blood flow to the vessel V.

Figure 3K:
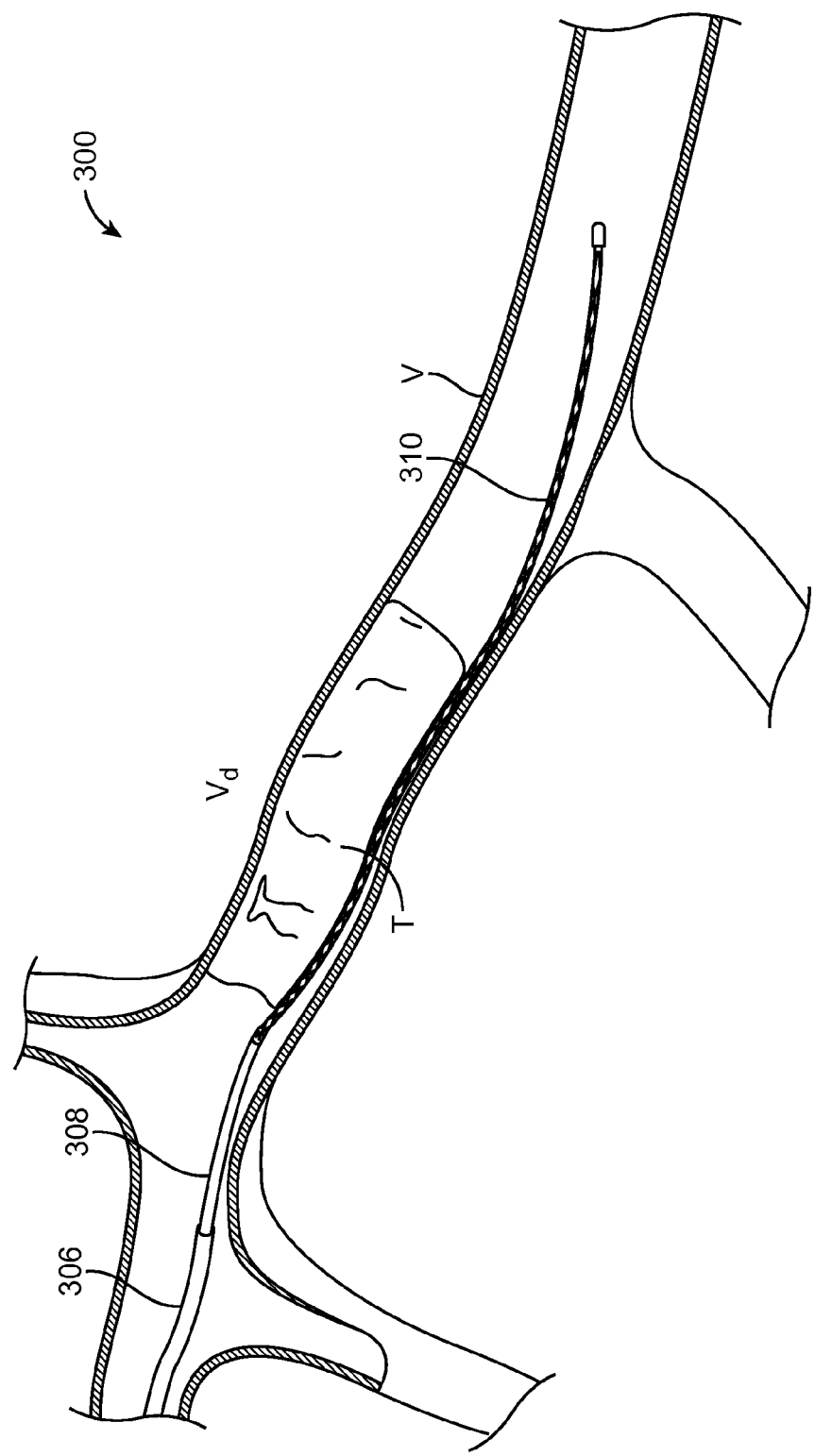
FIG. 3K is a cross-sectional view of a distal vessel portion illustrating a portion of a method for removing a thrombus, according to an embodiment of the invention.

FIG. 3K illustrates an alternate manner in performing the method 300. The method 300 can be performed according to what is shown and described with respect to FIGS. 3A and 3B, however, in some cases, the microcatheter 306 is too large to access the thrombus T. Accordingly, the microcatheter 306 may not fully advance to the distal vessel portion $V_d$ as shown in FIG. 3C, and remains in the proximal vessel portion $V_p$, or some position past the distal vessel portion $V_d$ but still proximal to the thrombus T.

In such cases, the microcatheter 306 can be advanced as forward as possible via the guidewire 312 (not shown), the guidewire 312 can be removed while the position of the microcatheter 306 is maintained. As shown in FIG. 3K, the elongated device 308 can then be advanced within the microcatheter 306 and distally beyond while being maintained in a contracted configuration, such that the expandable member 310 is not allowed to expand. This can be done, for example, by applying a distal force to pull-wire 312. The contracted expandable member 310 can then be advanced into at least a portion of the thrombus T, similar to how the guidewire 312 can be advanced as shown in FIG. 3B. After the expandable member 310 has been sufficiently placed within or axially co-adjacent with the thrombus T, the method can continue as shown in FIGS. 3E-3J.

Figure 3L:
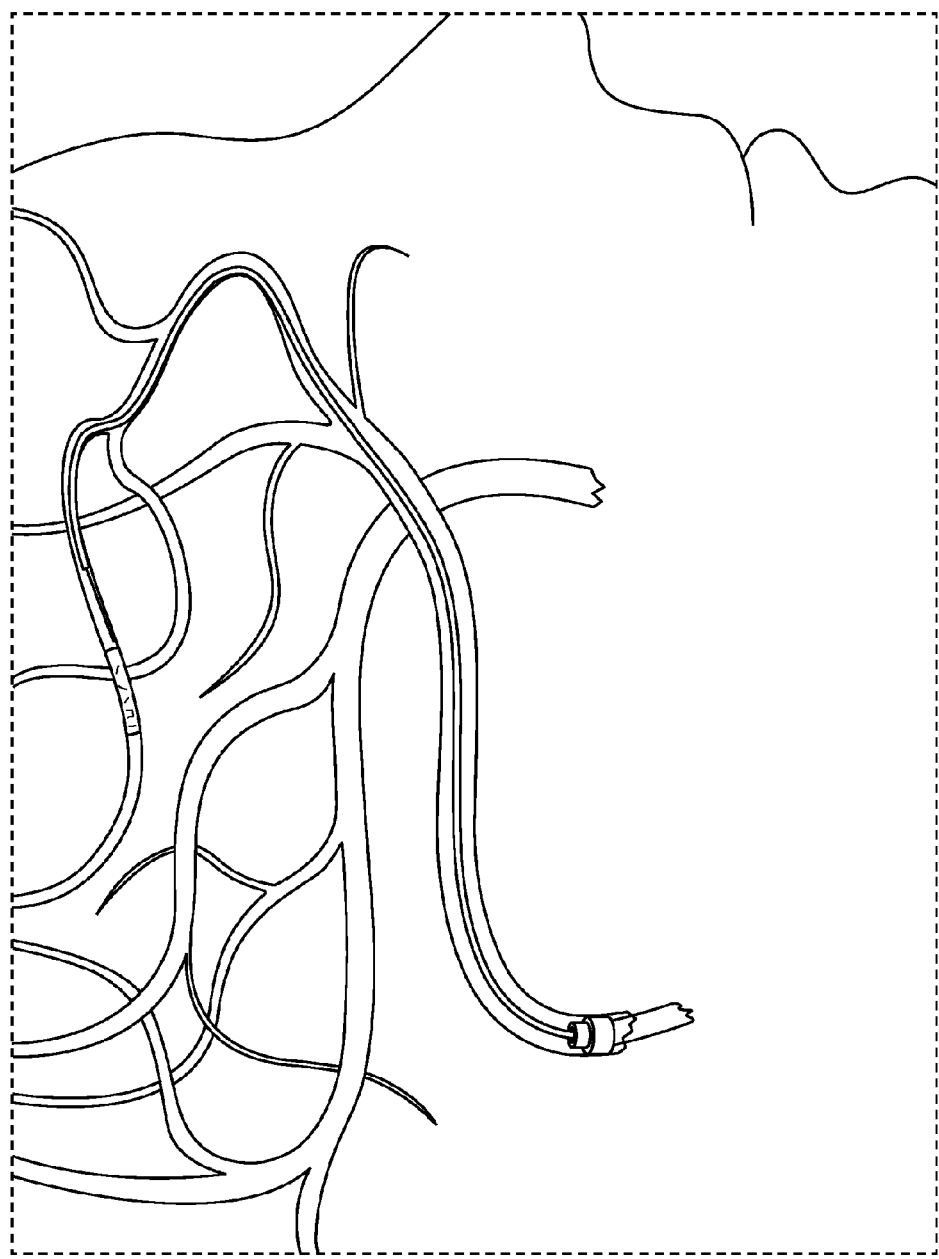
FIGS. 3L and 3M are cross-sectional overviews of the method depicted in FIGS. 3B-3J.
Figure 3M:
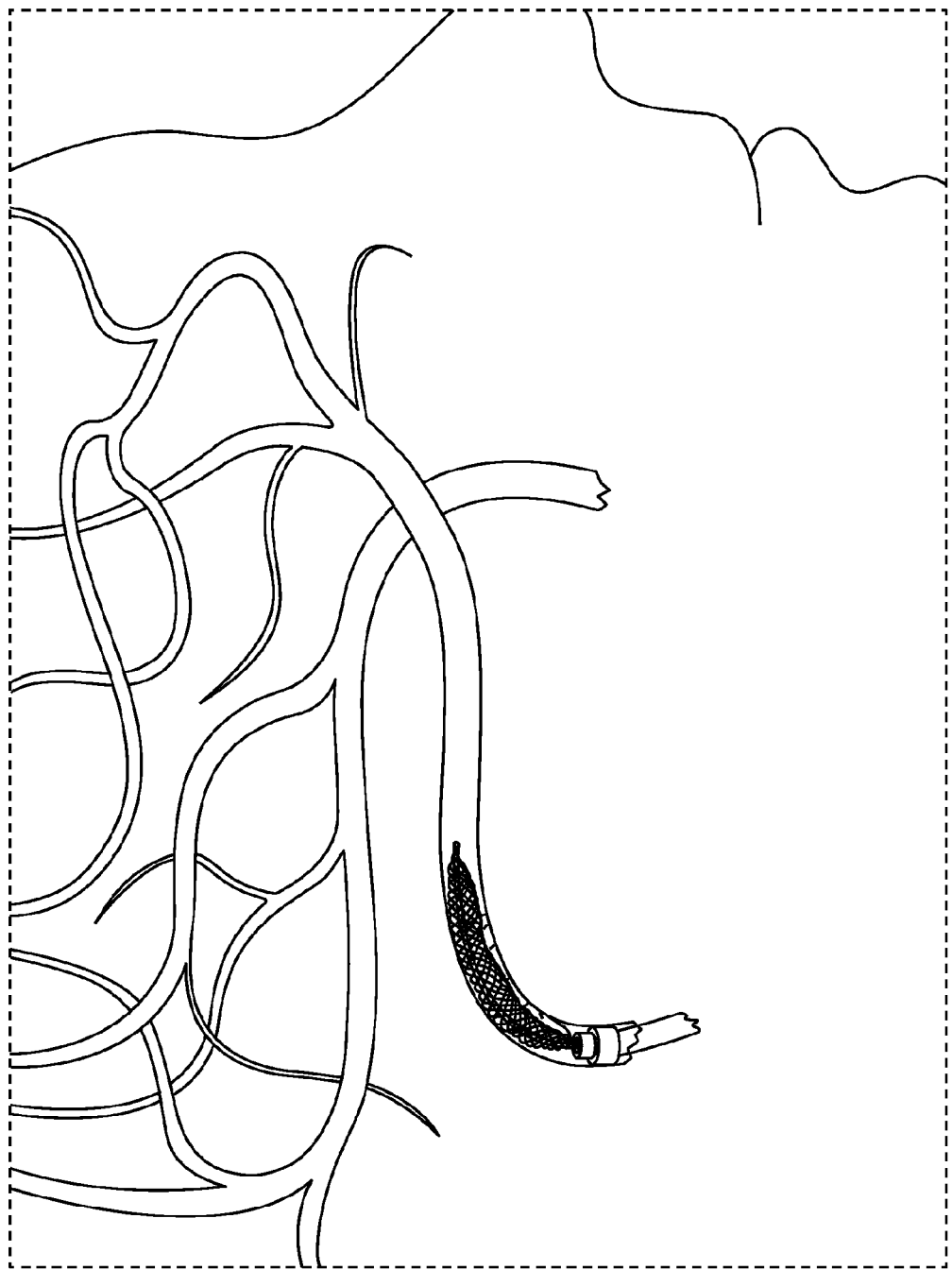

FIGS. 3L and 3M respectively show before and after overview figures of the method 300. As shown, the vessel anatomy is very torturous and includes vessel portions which increase in diameter and/or turn sharply. Such vessel portions present unique challenges to removal of the thrombus. For example, increases in vessel diameter can cause a prior retraction device to disengage from the thrombus T due to lessened expansion force. Further, sharp changes in direction can cause a prior retraction devices to kink and disengage from the thrombus T. Embodiments of the invention overcome these challenges by maintaining fixed engagement with the thrombus T when the vessel increases in diameter and/or sharply changes direction.

It should be understood that the relative vessel positions shown in the figures are scaled for ease of understanding and are not requirements for the locations of the proximal vessel portion $V_p$, distal vessel portion $V_d$, and intermediate vessel portion $V_i$. In some cases, these positions can be separated by a few millimeters of one another. Rather, these positions represent areas of the vasculature where articulation of the expandable member 310 is required to maintain axially fixed engagement with the thrombus.

Figure 4:
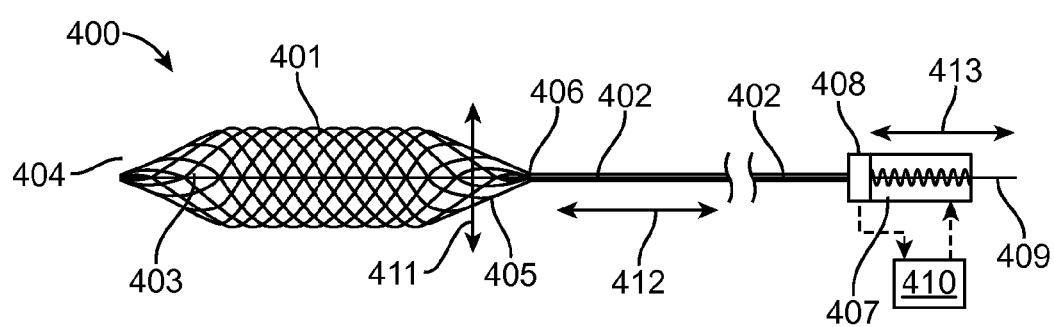
FIG. 4 is a cross-sectional view of the device, according to an embodiment of the invention.

Referring now to FIG. 4, the device 400 may contain a nitinol braided mesh 401. It may also contain an outer tube 402 and a push/pull inner wire 403. The braided mesh distal end 404 is connected to the inner push/pull wire 403. The braided mesh proximal end 405 is connected to the outer tube 402 near area 406. The mesh device 400 can also be made from a laser cut nitinol tube.

The basic mode of operations is when the outer tube 402 is held without movement and the inner push/pull wire 403 is pulled outwards the outer tube 402 the mesh expands (i.e. the diameter increases).

When the outer tube 402 is held without movement and the inner push/pull wire 403 is pushed towards the outer tube the mesh contracts (i.e. the diameter decreases).

The device properties may include a: a) one-to-one or other linear correspondence between the axial force 412 applying on the push/pull wire 409 and the radial force 411 applying by the mesh on the artery wall and/or the clot; and b) one-to-one or other linear correspondence between axial location of the push/pull wire and the mesh diameter.

These two device properties are described in detail in PerFlow Device Forces Analysis v1.1.doc. One-to-one correspondence between the axial and the radial force is given by equation 13 (shown below). One-to-one correspondence between push/pull wire axial location and the mesh diameter is given by solving first equation 2 to find mesh braiding angle β and then solving equation 2 for mesh diameter D.

Both device properties above are characterized by one-to-one correspondence determine or monitoring the in artery device condition, geometric and force, by the device out of the body portion. The device can use these properties in order to control the device radial force 411 according artery diameter and physician decision.

A spring may be used as an "axial force generator" 407. The spring can provide several "force versus spring" position characteristics. One alternative is constant radial force applying by the mesh 401 on the clot at every artery diameter. The constant force can be adjusted out of the body by pre loading the "axial force generator" 407 spring. Another alternative is non-constant force applying by the mesh on the clot at every artery diameter. The non-constant initial force can be adjusted out of the body by pre loading the "axial force generator" spring.

A hydraulic piston may be used as an "axial force generator" 407. The axial force is proportional to the hydraulic pressure. Hydraulic pressure may remain constant or controlled by close loop apparatus that received its input from displacement sensor 408 mounted between the outer tube 402 and the wire 409. This displacement (i.e. movement) 413 has one-to-one correspondence with the mesh diameter. Using the device 400, one-to-one correspondence between the axial force applying on the wire 409 and the radial force applying by the mesh, may benefit by configuring the controller 410 so as to provide an appropriate pre-defined hydraulic pressure by the hydraulic "axial force generator" that results in appropriate pre-defined mesh radial force versus artery diameter.

An electro mechanic means (or mechanism) may be used as an "axial force generator". The electro mechanic axial force may be constant or controlled by close loop apparatus that received its input from displacement sensor mounted between the outer tube and the wire. This displacement has a one-to-one or other linear correspondence with the mesh diameter. Using the device, one-to-one correspondence between the axial force applying on the wire and the radial force applying by the mesh, may benefit by configuring the controller so as to provide an appropriate pre-defined electro mechanic "axial force generator" that results in appropriate pre-defined mesh radial force versus artery diameter.

The axial mesh force may be controlled by the physician according its observation during the procedure by changing the "axial force generator" forces, using axial force generator controller that is controlled by one hand, lag or finger.

The Procedure

Figure 5A:
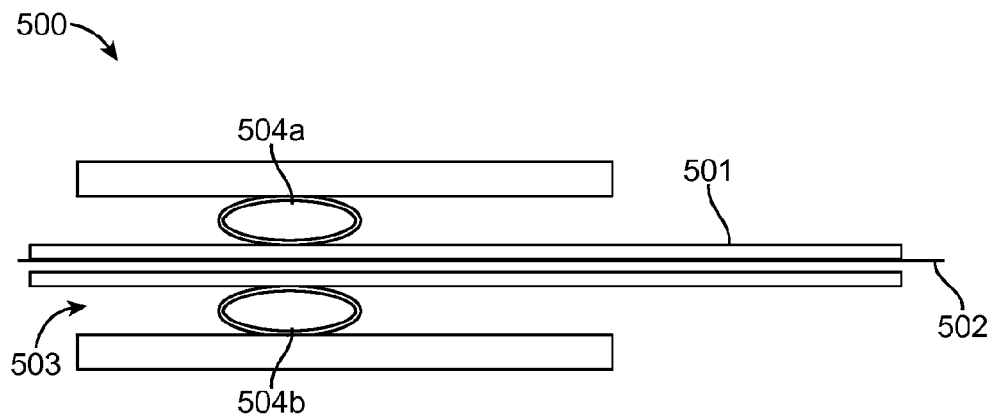
FIG. 5A is a cross-sectional view of a guide wire and micro catheter across a clot, according to an embodiment of the invention.
Figure 5B:
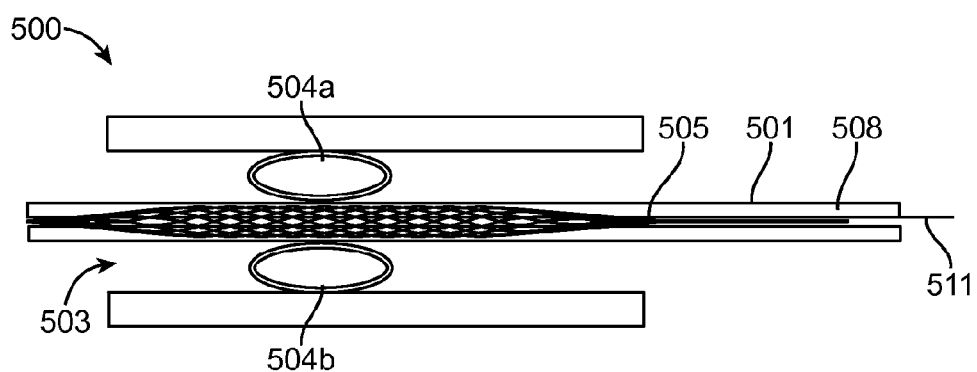
FIG. 5B is a cross-sectional view of the device inside the micro catheter, according to an embodiment of the invention.
Figure 5C:
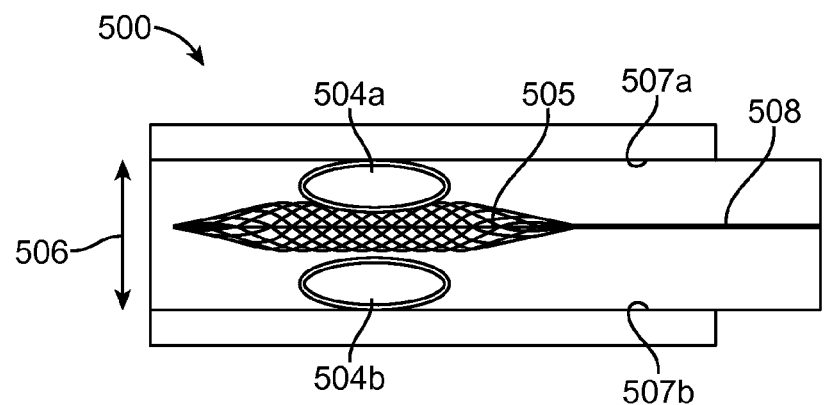
FIG. 5C is a cross-sectional view of the device expanded into the clot at ⅓-½ of the artery diameter to allow perfusion, according to an embodiment of the invention.

With reference to FIGS. 5A-5D, a microcatheter 501 over a guide wire 502 is introduced into the neuro vasculature 503. The guide wire 502 crosses the clot 504a, 504b and then the microcatheter 501 crosses the clot 504a, 504b over the guide wire 502 shown in FIG. 5A. The wire 502 is pulled out and the device is introduced into the microcatheter 501 shown in FIG. 5B. The device reaches the distal end of the microcatheter 501 and then the microcatheter is pulled back and unsheathes the device. The axial mesh 505 expands to ⅓-½ of the artery diameter 506 as shown in FIG. 5C. In this state the device allows perfusion (i.e. acute perfusion).

Acute Perfusion

When the device is deployed, blood flow is restored. That is beneficial for thrombus lysis, removal and clinical improvement.
 a. When the device is deployed, blood flow should be restored, even if partially and/or temporarily.
 b. When blood flow is restored, the oxygen-rich blood flows across the thrombus and immediately to the distal beds. This helps the ischemic, stunned (penumbra) region of the brain to start the process of restoring itself.
 c. The blood carries oxygen and nutrients to the brain, and takes away carbon dioxide and cellular waste. Blood flow protects against the cerebral atrophy and neuronal degeneration induced by the neuro chemical processes and pathways known to regulate cell death and atrophy after an ischemic even.
 d. This nutrient rich blood, when downstream, will lyse or enzymatically digest, any fragments of thrombus that breakaway from the large, proximal occlusion.
 e. Flowing blood across the large, proximal occlusion, softens the thrombus causing the device to expand further into the thrombus, improving the engagement and aiding in removal of the thrombus.
 f. Most thrombus are highly erythrocytic (i.e. contains alot of red blood cells). These lyse quickly when in blood flow, exposing the fibrin-rich portion of the thrombus. Blood flow has plasminogen in it. This can begin to break apart the fibrin matrix.

Mesh Expansion

The mesh 401 can further expand by keeping the outer tube 402 in place and pulling the push/pull wire 409 as shown in FIG. 4. Expanding the mesh secures the clot 504a and/or 504b between the mesh 505 and the artery wall(s) 507a and/or 507b, respectively as shown in FIG. 5C and % D. Pulling the clot out of the arterial system is done by pulling the outer tube 508 while constantly maintaining the mesh radial force on the clot to keep it secured the mesh. The stent cell pattern may physically grab the clot using a shortening of the device in to the clot. This may allow better anchoring of the braid in to the clot (as opposed to alternative devices that simply rely on the friction from the chronic outward force to push the clot against the vessel walls). This cell design, which allows the device to physically grab clot while minimizing maceration, may be braided using 50-60 micron wires that are round-shaped (because the mesh is not laser cut) as contrasts with alternative devices where the mesh elements are (wire-cut and) not round.

Figure 5D:
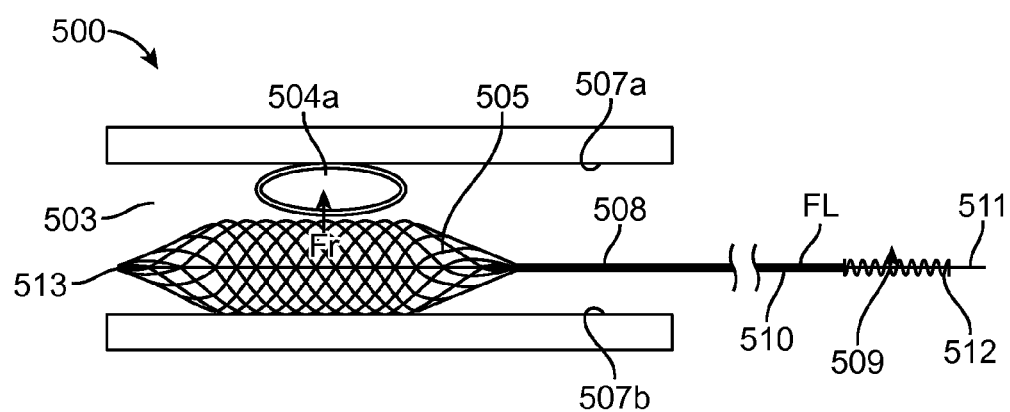
FIG. 5D is a cross-sectional view of the device including the expanded mesh with the clot secured between the mesh and the artery wall, according to an embodiment of the invention.
Figure 6:
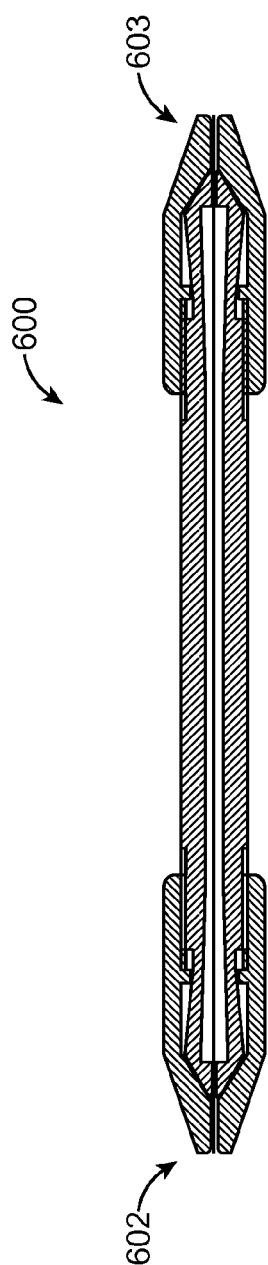
FIG. 6 is a cross section of a locking mechanism according to an embodiment of the invention.

The control of the radial force can be done by:
 i.) The physician using standard catheterization methods using fluoroscopy:
  a. Adjustment of the desired level of radial force by manipulating the push/pull wire.
  b. Locking Mechanism—a mechanical mechanism 601, shown in FIG. 6, includes a distal end 602 and a proximal end 603 and may be used to lock and secure the position of the elongate device 308 relative to the pull-wire 312. This allows the diameter to be fixed and/or dialed up or down. The Locking mechanism is a double end chuck that on the distal end grips the elongate device 308 and on the proximal end grips the pull-wire 312. Many optional gripping methods like collet chuck type, tapper slider, sloping segment. actuated either by rotating or shifting as known in the medical catheterization art of guide wire torque devices.
 ii.) The proximal part of the pull wire can be a stretchable wire or rub through rollers or use a set of cogwheels. That way, there will be a long and more controllable movement between the pull wire and the hypotube.
 iii.) Utilize a compensation mechanism that maintains the radial force:

a. The compensation mechanism 509 (FIG. 5D) can be a part of the device or an add on to the proximal end of the device.
b. One possible compensation mechanism is a compression spring located between the outer shaft 510 and the push/pull wire 511 (FIG. 5D). Without this spring pulling the outer tube back it will result in decrease of the mesh diameter (e.g. the opposite of pulling the wire).
c. Pulling the outer tube back having the compression spring located between the outer shaft 510 and the push/pull wire 511 will do two things. First the spring 512 will apply axial force on the push/pull wire 511 and by that an outwards radial force on the mesh. Second, when pulling the outer tube 510, it will pull the push/pull wire 511 and the mesh 505 connected to both outer tube 510 and pull the push/pull wire 511, by that it will pull the clot 504a out of the vasculature 503 keeping it secured between the mesh 505 and the artery wall 507a. This is possible even when the artery diameter 506 increases during the pull back of the device and/or system 500.
d. For the above, one can use a compression spring 512 (spring rate of ~0.0028 N/mm), or a clutch (i.e. electromagnet, friction, etc.) or even another braid or superelastic laser cut nitinol tube.

Distal Tip Options

The distal tip 513 needs to be atraumatic and/or flexible in order not to damage the vessel wall 507a, 507b. This can be accomplished by radiopaque polymers and/or by a platinum micro coil. Can be manufactured from one of the braid wires, laser cut nitinol tube, or polymer coated end of the mesh with the distal marker.

Figure 7A:
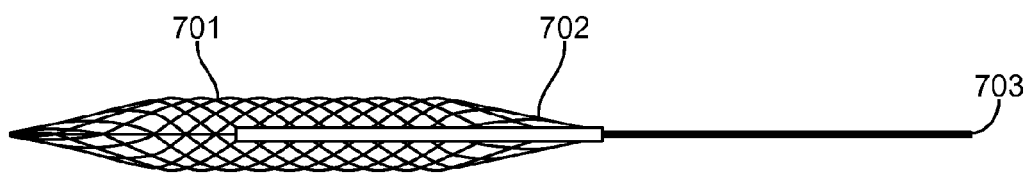
FIG. 7A is a cross-sectional view of the stopper in one configuration, according to an embodiment of the invention.
Figure 7B:
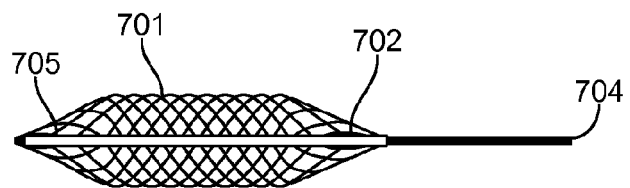
FIG. 7B is a cross-sectional view of the stopper in a configuration different from FIG. 7A, according to an embodiment of the invention.

Mesh—Tube Connection Options
1. Laser welding
2. RF welding
3. Gluing
4. Heat bonding Stopper Referring to FIGS. 7A and 7B, the mesh 701 can be expanded to a pre-defined maximum diameter utilizing a tube (i.e. stopper) 702 in the mesh 701 on the pull/push wire 703 that is connected to the proximal end 704 of the mesh.

Alternative Designs of the Mesh

In addition to the mesh comprised of 8-24 wires, the device can be built in the following variations:
Laser cut nitinol tube—closed cell
Etching and welding
Alternative braiding patterns
In addition the braid can be made with additional radio opaque wires.
In addition the braid can be made with flat wires in order to use less wires but stable structure.
In addition the braid can be made with flat wires that lay in a perpendicular position in order to cut into the clot.
The braid can be heat set to an open maximum diameter (4 mm), or to a collapsed position (0.5 mm) or middle position (1.5 mm). then when the device initially expands it will be at the set position.
One possible configuration is to make the system at the at rest position look and act like a guide wire with diameter of 0.014" to 0.018" by that just with the micro catheter the device will penetrate the clot, then the rest of the procedure will be exactly as before.
The braid device can be manufactured as a long device (longer than 30 mm shorter than 100 mm). The physician will un sheath the micro catheter from the device for a length suitable for clot removal according to clot length. It can be clot length+20 mm for example.

Clot Extraction

Inner shaft is pulled axially, the device is axially shortened and expand further radially due to the relation between device length L and diameter D (see Equation 3 below). Device struts applies radial force (or pressure) on the elastic clot against the artery wall. At this stage the clot is secured between the struts and the artery wall can safely extract by pulling the all chatter proximally. Radial pressure P applying by the device is superposition the elastic pressure $P_r$ and the pressure applied from the axially movement PL $P=P_r+P_L$.
a. $P_r$ is defined by Equation 14 or Equation 17, device initial geometry (Do and βo) and artery diameter as D. Note that in case that D>Do, $P_{ei}$ value is negative.
b. $P_1$ may be found by applying the same energy approach describing in Equation 8 to Equation 13, while axial force F is the shaft force.

Geometrical Properties

The relation between nominal and free position geometry is given by Equation 1:

$$D = \frac{D_0\cos(\beta)}{\cos(\beta_0)} \qquad \text{Equation 1}$$

$$L = L_0 + \delta = L_0\left(\frac{\sin(\beta)}{\sin(\beta_0)}\right) \qquad \text{Equation 2}$$

Do, Lo and βo are free position average diameter, length and pitch angle. D, L and β are nominal (implanted) average diameter length and pitch angle.

Dividing Equation 2 by Equation 1 yields a simple relation between device length L and diameter D and:

$$\frac{L}{D} = K_0\tan(\beta) \qquad \text{Equation 3}$$

$$K_0 = \frac{L_0}{D_0\tan(\beta_0)}$$

Equation 3 sows that it is possible to control the device diameter D by manipulate device L and vice-versa.

Mechanical Properties

From the equation for the load action on an open-coiled helical spring with the ends free to rotate it may be shown that the axial load F action on the device is given by Equation 4:

$$F = 2Nw * \left(\frac{GI_P}{k_3}\left(\frac{2\sin\beta}{k_3} - k_1\right) - \frac{EI\tan(\beta)}{k_3}\left(\frac{2\cos\beta}{k_3} - k_2\right)\right) \qquad \text{Equation 4}$$

Where $k_1$, $k_2$, $k_3$ are constants, determined by the free position geometry, given by Equation 5:

$$k_1 = \frac{\sin(2\beta_0)}{D_0} \quad k_2 = \frac{2\cos^2(\beta_0)}{D_0} \quad k_3 = \frac{D_0}{\cos(\beta_0)} \qquad \text{Equation 5}$$

I and Ip are the moment of inertia and polar moment of inertia of the wire, respectively.

For a circular cross section wire with diameter d, I and Ip are given by Equation 6:

$$I = \frac{\pi d^4}{64} \text{ and } Ip = 2I = \frac{\pi d^4}{32} \quad \text{Equation 6}$$

E and G are material mechanical properties modulus of elasticity and the modulus of rigidity respectively. βo and β are free and nominal pitch angles. Nw is total number of filaments. For design purposes it is convenient to express the axial load F in terms of the device nominal diameter D and free position parameters. The explicit expression for axial the load F of the device made by round cross section filaments Equation 7:

$$F = \frac{\pi N w \cos^2 \beta_0 d^4}{16 D_0^2} * \left( 2G \left\{ \sqrt{1 - \left( \frac{D}{D_0} \cos \beta_0 \right)^2} - \sin \beta_0 \right\} - E \left\{ \left( \frac{D}{D_0} - 1 \right) \sqrt{\left( \frac{D_0}{D} \right)^2 - \cos^2 \beta_0} \right\} \right) \quad \text{Equation 7}$$

The average radial pressure $P_a$ is calculated by the use of the energy equation. Consider a suction of the of the length L and diameter D in an arbitrary position. Under the action of axial force F, the device extends by an incremental length dL and decreases in diameter by an incremental length dR (D=2R), so that the energy dW is given by:

$$dW = FdL \quad \text{Equation 8}$$

We can also produce the same deflection dL and dR by applying a radial pressure Pa to an imaginary wall around the device, action over an area mDL, so that the energy dW is given by:

$$dW = Pa\pi DL dR \quad \text{Equation 9}$$

The equating of (Equation 8) and (Equation 9) yields:

$$Pa = \frac{2F}{\pi DL} \frac{dL}{dD} = \frac{2F}{\pi DL} \frac{dL}{d\beta} \frac{d\beta}{dD} \quad \text{Equation 10}$$

Since D is explicit function of β, using Equation 1, replacing $\beta_0$ and $D_0$ by β and D in an arbitrary position.

$$\frac{d\beta}{dD} = \left( \frac{dD}{d\beta} \right)^{-1} = -\frac{\cos(\beta_0)}{D_0 \sin(\beta)} = -\frac{1}{k_3 \sin(\beta)} \quad \text{Equation 11}$$

And using Equation 2, replacing δ by dL:

$$\frac{dL}{d\beta} = \frac{\pi c D_0 \cos(\beta)}{\cos(\beta_0)} \quad \text{Equation 12}$$

And thus $$Pa = -\frac{2Fc}{DL\tan(\beta)} = \frac{2F}{\pi D^2 \tan^2 \beta} \quad \text{Equation 13}$$

Local radial pressure is the load supported by the Perflow device assuming imaginary surface equal to the blocked area around the device: πDL/(1−PI)

$$P_L = \frac{Pa}{(1 - PI)} \quad \text{Equation 14}$$

Approximation of the device PI can be performed using the following simplified equation:

$$PI[\%] \approx 100 * \left( \frac{W_N^2 \sin \alpha}{W_N^2 \sin \alpha + 2Wd + d^2} \right) \quad \text{Equation 15}$$

Where Wn is given by:

$$W_N = \frac{\pi D_N}{N_W \cos(\beta_N)} - \frac{d}{\sin(2\beta_N)} \quad \text{Equation 16}$$

For design purposes it is convenient to express the average radial pressure in terms of diameters D. The explicit expression for the average radial pressure of device made of round cross section (diameter d) filaments is as follows:

$$Pa = \frac{Nw \cos^4 \beta_0 d^4}{8 D_0^4 \left[ 1 - \left( \frac{D}{D_0} \cos \beta_0 \right)^2 \right]} * \left( 2G \left\{ \sqrt{1 - \left( \frac{D}{D_0} \cos \beta_0 \right)^2} - \sin \beta_0 \right\} - E \left\{ \left( \frac{D}{D_0} - 1 \right) \sqrt{\left( \frac{D_0}{D} \right)^2 - \cos^2 \beta_0} \right\} \right) \quad \text{Equation 17}$$

This is the equation for device elastic radial pressure and will be marked later also as $P_{el}$. One can convert from the initial pitch angle βo to the initial braid angle αo in Equation 7 and Equation 17 by using the relation βo=π/2−αo/2

"Radial force" is a value that can be presented in measurement methods like the Thin Film Test. In this test a measurement of changes in diameter vs. force is performed while the device is circumferentially compressed through 360 degrees. Radial force Fr in force per unit length can be calculated following Equation 17 result by Equation 18:

$$Fr = \frac{Pa}{\pi D} \quad \text{Equation 18}$$

Additional Applications

Open blocked vessels below the knee.

Utilize any of the devices described herein, as a balloon for the opening of cervical narrowed arteries with no need to stop the blood flow, and/or while maintaining control of the radial force.

For use as a temporary aneurysm neck bridge during aneurysm occlusion with embolization coils. Balloons may be used to perform 'aneurysm neck remodeling' if a stent cannot be used, typically in ruptured aneurysm treatments. When using balloons to remodel the aneurysm neck, flow arrest typically results. With the devices described herein, 'neck remodeling' may be performed preventing coils from entering the parent artery without flow arrest. Risk of ischemic stroke may be mitigated.

For use as a cerebral vasospasm treatment during hemorrhagic stroke or arterial damage. Balloons may be used during this procedure. Medical therapy is also performed (nimodipine and/or verapimil). With the devices described herein, 'angioplasty' of the vasospastic vessel may be performed without flow arrest. Risk of ischemic stroke may be mitigated.

Additional Aspects of Therapy System and Use

When treating an occlusion in a small, delicate cerebral blood vessel, there may be significant clinical advantages to limiting the number of intravascular structures advanced to the occlusion, providing accurate control over (and as possible, limiting the number of) engagement motions between the intravascular devices and the occlusion (and/or the adjacent vessel wall), and limiting the total time during which the vessel is subjected to intravascular devices during an overall treatment.

Prior to advancement of a therapy device to the occlusion, contrast imaging may help indicate a location of an occlusion and provide an indication of a length of the overall occlusion.

Identified occlusions may include more than one material, and often include very different embolic materials having differing properties. Prior to accessing the occlusion, imaging may not accurately indicate the locations and/or sizes of the structures making up an overall occlusion.

Preferred treatments for addressing differing occlusions may differ significantly based on both materials forming the occlusions and sizes of the structures formed by those materials.

Advantageously, the devices described herein can facilitate one-pass (or near one-pass) therapies, where only a single treatment device is advanced along a guidewire extending across the occlusion. Gentle and controllable expansion of the device under image guidance can help characterize the occlusion material to the user, and can then also be used to apply the appropriate therapy in response.

Engagement of the device with the occlusive material may indicate that much or all of the occlusion comprises a soft, relatively benign material. That material may, in some cases be subject to lysing (with or without lysing agents) after being gently and controllably broken up by relative movement of the push-pull wire and the outer tube.

Optionally, maceration of some or all of the occlusive materials can be performed by gentle expansion and contraction of the device using the push/pull members, without having to resort to repeated unsheathing an re-sheathing of the device (though such maceration via repeated unsheathing and re-sheathing can employ self-expansion for maceration in some embodiments.

Where appropriate, after maceration of much of an occlusion that is formed of soft material a small remaining solid thrombus structure can be held against the vessel wall and dragged proximally to a capture device by safely expanding the device to a size that applies a desired engagement force.

Engagement of the device with the occlusive material may indicate that much or all of the occlusion comprises a tough resilient material. Controlled expansion of the device to engage and pull the solid thrombus wall proximally may be limited to avoid excessive device/wall and/or thrombus/wall engagement, etc.

The distal end of the device can be viewed as a distal particle catch that reduces the incidence of procedural distal emboli (PDE) and improves clinical outcomes. The SWIFT trial noted some instances of distal emboli for alternative devices, and decreasing PDE may improve potential outcome for thrombectomy devices in acute stroke care. The distal end of the device that is post the clot keeps to the diameter of the vessel so any particle that is broken off the clot has a high chance of not passing the distal end.

While the exemplary embodiments have been described in some detail for clarity of understanding and by way of example, a number of modifications, changes, and adaptations may be implemented. Further, any dimensions mentioned are exemplary guidelines for one skilled in the art, and thus do not necessarily represent limitations as to size and/or proportion of embodiments of the invention.

What is claimed is:

1. A device for compressing and removing a thrombus to increase blood flow through a vessel, the device comprising:
    an outer tube having a proximal end and a distal end, the tube sized to be slidably disposed within a microcatheter, the tube having an expandable member adjacent the distal end;
    a push/pull wire slidably disposed within the outer tube, the wire having a proximal end and a distal end, the wire configured to be actuated from outside the body, the wire coupled to the expandable member at the distal end of the expandable member;
    wherein the expandable member is configured to be increased in diameter to a first larger diameter and a portion of said expandable member is configured to exert a radial force sufficient to fixedly engage the expandable member to a surface of the thrombus by compression of the thrombus between said portion of said expandable member and a vessel wall, when an axial force component is applied by a user to the proximal end of the wire by pulling the wire, said portion of said expandable member further configured to exert an axial force to the fixedly engaged surface of the thrombus, wherein said radial and axial forces in combination at said portion of said expandable member comprise an engagement force sufficient to move the entire thrombus along the vessel wall;
    wherein said expandable member comprises a plurality of helical wires defining a helical diameter that expands to non-uniformly compress the thrombus according to a slope angle representing a degree of a wire to the thrombus engagement, said non-uniform compression causing portions located between said fixedly engaged surfaces of the thrombus in contact with said wires to arc towards a center axis of the vessel according to said slope angle; said wires are moveable with respect to one another between a proximal end and a distal end of said expandable member.

2. The device of claim 1, wherein the expandable member is configured to be decreased in diameter when an axial force component is applied by the user to the proximal end of the wire by pushing the wire.

3. The device of claim 1, wherein the expandable member is further configured to expand to a second diameter that is larger than the first diameter in order to maintain or increase the slope angle.

4. The device of claim 1, wherein the expandable member is configured to expand to approximately 6 mm in diameter in a maximally expanded state.

5. The device of claim 1, wherein the wires are configured to not cut into the thrombus upon expansion, thereby maintaining or increasing the slope angles during expansion of the expandable member.

6. The device of claim 1, wherein an amount of radial force exerted by the expandable member is increased or maintained as the vessel diameter increases in size to maintain the engagement with the thrombus.

7. The device of claim 1, wherein the radial force is a constant force.

8. The device of claim 1, wherein the radial force is a non-constant force.

9. The device of claim 1, wherein the expandable member is configured to be decreased in diameter when an axial force component is applied by the user to the proximal end of the tube by pulling the tube.

10. The device of claim 1, wherein a displacement sensor is mounted between said outer tube and said wire.

11. The device of claim 1, wherein a stopper in the form of a tube is configured on said wire, said stopper limiting movement of said wire to limit expansion of said expandable member to a predefined diameter.

12. The device of claim 1, wherein a clutch is located between said outer tube and said wire.

13. The device of claim 1, wherein a distal end of the expandable member is configured to pierce the thrombus.

14. The device according to claim 1, wherein said expandable member comprises between 8-24 coiled and interwoven wires braided into a basket-like structure.

15. The device according to claim 1, wherein if expanded outside the vessel, said expandable member is configured to expand to a substantially uniform diameter.

16. The device according to claim 1, wherein said expandable member is shaped and sized to remove a thrombus from a small intracranial blood vessel.

17. The device according to claim 1, wherein said radial force comprises a minimal force required to prevent the thrombus from sliding off during withdrawal.

18. The device of claim 1, wherein said radial force is sufficient to allow displacement of the thrombus along the vessel wall by axial displacement of said expandable member.

19. The device of claim 1, wherein said radial force is sufficient to maintain engagement between said portion of said expandable member and the surface of the thrombus when the thrombus is moved along the vessel wall by said portion of said expandable member.

20. The device of claim 1, wherein said radial force applied to the surface of the thrombus by said portion of aid expandable member is sufficient to overcome a frictional force between the thrombus and the vessel wall.

21. The device of claim 1, wherein said radial force applied to the surface of the thrombus is in the range of from 215 to 1681 Pa.

22. The device of claim 1, wherein said wires are spirally wrapped and woven wires.

23. The device according to claim 1, wherein said plurality of wires is configured to expand to non-uniformly compress the thrombus along an axis through the thrombus when applying said first engagement force.

24. The device according to claim 1, wherein said expandable member does not cut but compresses the thrombus.

25. The device according to claim 1, wherein the axial force component is provided by a spring located at a proximal end of the wire and coupled to the wire.

26. The device of claim 25, wherein the spring provides, by pre-loading the spring, several spring versus force positions in which a radial force applied by the expandable member on the thrombus is adjusted.

27. The device according to claim 25, wherein said expandable member is configured to apply a constant radial force on said thrombus at every artery diameter, said constant force adjustable out of the body by preloading said spring.

28. The device according to claim 25, wherein said expandable member is configured to apply a non-constant radial force on said thrombus at a plurality of artery diameters, said non-constant force adjustable out of the body by preloading said spring.

29. The device according to claim 1, wherein the expandable member is configured to be increased in diameter from a natural state diameter to said first larger diameter.

30. The device of claim 29, wherein wires of the expandable member are coiled and interwoven, and are configured to expand to approximately ⅓ to ½ of the vessel diameter in the natural state diameter.

31. The device of claim 1, wherein said plurality of wires are configured to divergently compress a thrombus within a vessel by application of a first engagement force to maximally compress thrombus portions in contact with the wires, wherein the first engagement force comprises the radial force component acting at the maximally compressed thrombus portions, and wherein during retraction the wires further apply an axial force component, and wherein the radial force component and axial force component together comprise a first moving engagement force.

32. The device of claim 31, wherein the axial force and the radial force represent a linear relationship, the radial force component comprising a majority of the first moving engagement force.

33. The device of claim 31, wherein the axial force and the radial force represent a one-to-one correspondence provided by the equation:

$$Pa = -\frac{2Fc}{DL\tan(\beta)} = \frac{2F}{\pi D^2 \tan^2 \beta}$$

where:
Pa=average radial pressure
F=axial force
L=device length
D=device diameter.

34. The device of claim 1, wherein in a natural state the expandable member has a continuously curved profile formed between proximal and distal ends.

35. The device of claim 34, wherein a total of 8 wires are interwoven to form the expandable member, and wherein axial distance between the crossed wires longitudinally is approximately 3.5 mm when the expandable member is expanded to 2 mm in diameter, and wherein axial distance between the crossed wires longitudinally is approximately 2.4 mm when the expandable member is expanded to 4 mm in diameter.

36. The device of claim 34, wherein a total of 16 wires are interwoven to form the expandable member, and wherein axial distance between the crossed wires longitudinally is approximately 1.7 mm when the expandable member is expanded to 2 mm in diameter, and wherein axial distance between the crossed wires longitudinally is approximately 1.2 mm when the expandable member is expanded to 4 mm in diameter.

37. The device of claim 34, wherein a total of 24 wires are interwoven to form the expandable member, and wherein axial distance between the crossed wires longitudinally is approximately 1.1 mm when the expandable member is expanded to 2 mm in diameter, and wherein axial distance between the crossed wires longitudinally is approximately 0.8 mm when the expandable member is expanded to 4 mm in diameter.

38. The device of claim 34, wherein pull wire actuation distance to expandable member diameter ratio ranges from approximately 0.4 at the first diameter to 2.8 at a maximal diameter.

\* \* \* \* \*